US012758143B2

(12) United States Patent
Wilson et al.

(10) Patent No.: US 12,758,143 B2
(45) Date of Patent: Oct. 13, 2026

(54) SYSTEMS AND METHODS FOR PRESENTING COMPLEX MEDICAL CONDITION DIAGNOSES

(71) Applicant: Hologic, Inc., Marlborough, MA (US)

(72) Inventors: Kevin E. Wilson, Acton, MA (US); Thomas L. Kelly, Woburn, MA (US)

(73) Assignee: Hologic, Inc., Marlborough, MA (US)

( * ) Notice: Subject to any disclaimer, the term of this patent is extended or adjusted under 35 U.S.C. 154(b) by 185 days.

(21) Appl. No.: 18/607,883

(22) Filed: Mar. 18, 2024

(65) Prior Publication Data

US 2024/0260928 A1 Aug. 8, 2024

Related U.S. Application Data

(63) Continuation of application No. 16/062,547, filed as application No. PCT/US2016/067333 on Dec. 16, 2016, now Pat. No. 11,963,820.

(Continued)

(51) Int. Cl.

| | |
|---|---|
| ***A61B 5/00*** | (2006.01) |
| ***A61B 5/0522*** | (2021.01) |
| ***A61B 5/0536*** | (2021.01) |
| ***A61B 5/0537*** | (2021.01) |
| ***A61B 5/11*** | (2006.01) |

(Continued)

(52) U.S. Cl.

CPC .......... *A61B 5/4519* (2013.01); *A61B 5/0073* (2013.01); *A61B 5/0522* (2013.01); *A61B 5/0536* (2013.01); *A61B 5/0537* (2013.01); *A61B 6/03* (2013.01); *A61B 6/482* (2013.01); *A61B 6/50* (2013.01); *A61B 6/505* (2013.01); *A61B 6/5217* (2013.01); *A61B 6/5294* (2013.01); *G16H 50/20* (2018.01);

(Continued)

(58) Field of Classification Search

CPC ..... A61B 6/482; A61B 5/4519; A61B 5/0537; A61B 5/505; A61B 5/112; A61B 5/225; A61B 6/505

See application file for complete search history.

(56) References Cited

U.S. PATENT DOCUMENTS 6,081,582 A 6/2000 Mazess et al.
6,385,283 B1 5/2002 Stein et al.

(Continued)

OTHER PUBLICATIONS

Jentoft et al., "Sarcopenia: European consensus on definition of diagnosis: Report of the European Working Group on Sarcopenia in Older People", Age and Aging, 39: 412-423 (2010) (Year: 2010).*

(Continued)

*Primary Examiner* — Colin T. Sakamoto

(74) *Attorney, Agent, or Firm* — Merchant & Gould P.C.

(57) ABSTRACT

A method of generating a visual representation of a complex medical diagnosis includes receiving a first signal corresponding to a measurement of a patient biological condition. A second signal corresponding to a measurement of a patient performance condition is also received. The first and second signals are processed and a visual representation of a diagnostic assessment is generated. The diagnostic assessment is based at least in part on the patient biological condition and the patient performance condition. The visual representation is marked with the measurement of the patient biological condition and the measurement of the patient performance condition.

14 Claims, 18 Drawing Sheets

Related U.S. Application Data

(60) Provisional application No. 62/268,384, filed on Dec. 16, 2015.

(51) Int. Cl.
*A61B 5/22* (2006.01)
*A61B 6/00* (2024.01)
*A61B 6/03* (2006.01)
*A61B 6/50* (2024.01)
*G16H 50/20* (2018.01)

(52) U.S. Cl.
CPC ............... *A61B 5/112* (2013.01); *A61B 5/225* (2013.01); *A61B 5/4869* (2013.01); *A61B 5/4872* (2013.01)

(56) References Cited

U.S. PATENT DOCUMENTS

| | | | | |
|---|---|---|---|---|
| 6,740,041 | B2 * | 5/2004 | Faulkner | A61B 6/505 600/449 |
| 6,999,549 | B2 * | 2/2006 | Sabol | A61B 6/482 378/5 |
| 7,725,153 | B2 | 5/2010 | Kelly et al. | |
| 8,579,814 | B2 * | 11/2013 | Fotiades | G16H 10/60 705/2 |
| 8,792,689 | B2 | 7/2014 | Kelly et al. | |
| 9,179,873 | B2 | 11/2015 | Kelly et al. | |
| 9,642,585 | B2 | 5/2017 | Wilson | |
| 11,963,820 | B2 | 4/2024 | Wilson | |
| 2002/0042328 | A1 | 4/2002 | Yoo | |
| 2004/0077088 | A1 | 4/2004 | Charles, Jr. | |
| 2005/0015002 | A1 * | 1/2005 | Dixon | A61B 5/1038 600/595 |
| 2010/0234719 | A1 | 9/2010 | Kelly et al. | |
| 2011/0235886 | A1 | 9/2011 | Kelly et al. | |
| 2013/0245443 | A1 | 9/2013 | Karjalainen et al. | |
| 2014/0148733 | A1 | 5/2014 | Stone et al. | |

OTHER PUBLICATIONS

Joyce et al., "Association of Muscle Strength and Bone Mineral Density in Adult Survivors of Childhood Acute Lymphoblastic Leukemia" Archives of Physical Medicine and Rehabilitation, 92(6): 873-879 (2011) (Year: 2011).*

Cruz-Jentoft, A., et al., "Sarcopenia: European consensus on definition and diagnosis: Report of the European Working Group on Sarcopenia in Older People", Age and Ageing, 39: 412-423 (2010).

"Frailty", American Geriatrics Society, Geriatrics Evaluation & Management Tools, 2 pages (2012).

Dodds, Richard Matthew et al., "The Epidemiology of Sarcopenia", The Journal of Clinical Densitometry: Assessment & Management of Musculoskeletal Health, 1-6 (2015).

PCT International Search Report and Written Opinion of the International Searching Authority for International Patent Application No. PCT/US2016/067333 mailed Mar. 10, 2017, 8 pages.

Joyce, E. et al., "Association of Muscle Strength and Bone Mineral Density in Adult Survivors of Childhood Acute Lymphoblastic Leukemia", Archives of Physical Medicine and Rehabilitation, 92(6): 873-879 (2011).

McLean, R. et al., "Developing Consensus Criteria for Sarcopenia: an Update", Journal of Bone and Mineral Research, 2-15 (2015).

Ormsbee, M. et al., "Osteosarcopenic obesity: the role of bone, muscle, and fat on health", J. Cachexia Sarcopenia Muscle, 5: 183-192 (2014).

PCT International Preliminary Report on Patentability in International Application PCT/US2016/066907, mailed Jun. 19, 2018, 7 pages.

PCT International Preliminary Report on Patentability in International Application PCT/US2016/067333, mailed Jun. 19, 2018, 6 pages.

PCT International Search Report and Written Opinion in International Application PCT/US2016/066907, mailed Feb. 27, 2017, 8 pages.

Peel, N. et al., "Bone Mineral Density of the Hand in Rheumatoid Arthritis", Arthritis & Rheumatism, 37(5): 983-991 (1994).

Roberts, H. et al., "Current Clinical Care of Older Adults with Sarcopenia", Journal of Clinical Densitometry: Assessment & Management of Musculoskeletal Health, 1-6 (2015).

Verschueren, S. et al., "Sarcopenia and its relationship with bone mineral density in middle-aged and elderly European men", Osteoporos Int, 24: 87-98 (2013).

* cited by examiner

SYSTEMS AND METHODS FOR PRESENTING COMPLEX MEDICAL CONDITION DIAGNOSES

CROSS-REFERENCE TO RELATED APPLICATIONS

This application is a continuation of U.S. patent application Ser. No. 16/062,547, filed Jun. 14, 2018, now U.S. Pat. No. 11,963,820, which is a National Stage Application of PCT/US2016/067333, filed Dec. 16, 2016, which claims priority to and the benefit of U.S. Provisional Patent Application No. 62/268,384, filed Dec. 16, 2015. This application is also related to U.S. patent application Ser. No. 14/553,533, now U.S. Pat. No. 9,642,585, filed Nov. 25, 2014; as well as PCT Patent Application Serial No. PCT/US2016/019562, filed Feb. 26, 2016. The disclosures of each of the above applications are hereby incorporated by reference herein in their entireties.

INTRODUCTION

For example, as the population of older Americans, defined as persons aged 65 and older, grows in proportion to the total US population, it is increasingly important to better understand, diagnose, and treat complex age-related syndromes that affect this subset of the US population.

Examples of such complex syndromes that are of particular interest to professionals studying age-related syndromes are obesity, osteoporosis, sarcopenia, and frailty. Obesity is defined as a condition of excess weight, specifically adipose tissue, in the body, and osteoporosis is defined as a skeletal disorder characterized by compromised bone strength leading to increased risk of fractures. Sarcopenia is defined as low muscle mass combined with the loss of muscle strength and performance. Generally, sarcopenia is a geriatric syndrome and overlaps considerably with physical frailty.

As the knowledge base surrounding sarcopenia as a condition grows, so too does the definition change to match the knowledge base. As is currently understood in the field, sarcopenia is defined as the presence of low muscle mass and low muscle function. Low muscle function is understood as low muscle strength, low muscle performance or some combination of the two. Frailty is a clinical syndrome that encompasses weakness, low energy, slowed walking speed, decreased physical activity, and weight loss.

References directed to sarcopenia are identified below, the disclosures of each of which are incorporated by reference herein in their entireties:

DODDS, Richard Matthew et al., "The Epidemiology of Sarcopenia", Journal of Clinical Densitometry, 2015, pages 1-6.

MCLEAN, Robert R. et al., "Developing Consensus Criteria for Sarcopenia: an Update", Journal of Bone and Mineral Research, 2015, pages 2-15.

CRUZ-JENTOFT, Alfonso J. et al., "Sarcopenia: European Consensus of Definition and Diagnosis", Age and Ageing 2010, Vol. 39, 2010, pages 412-423.

ROBERTS, Helen C. et al., "Current Clinical Care of Older Adults with Sarcopenia", Journal of Clinical Densitometry, 2015, pages 1-6.

ORMSBEE, Michael J. et al., "Osteosarcopenic Obesity: the Role of Bone, Muscle, and Fat on Health", J Cachexia Sarcopenia, 2014, Vol. 5, pages 183-192.

American Geriatrics Society, "Frailty", Geriatrics Evaluation & Management Tools, 2012, 2 pages.

KELLY, Thomas L. et al., "Dual Energy X-ray Absorptiometry Body Composition Reference Values from NHANES", PLOS ONE September 2009: vol. 1, Iss. 9.

CHEN, Xujiao et al., "Frailty Syndrome: an Overview", Clin. Interv. Aging. Mar. 19, 2014; 9: 433-441 (available at http://www.ncbi.nlm.nih.gov/pmc/articles/PMC3964027/).

PALACE, Zachary J. et al., "The Frailty Syndrome", Today's Geriatric Medicine, Vol. 7, No. 1, P. 18 (available at http://www.todaysgeriatricmedicine.com/archive/012014p18.shtml).

Computed tomography (CT scan), magnetic resonance imaging (MRI) and dual energy x-ray absorptiometry (DXA) can all be used in the diagnosis of obesity, osteoporosis, and sarcopenia. Generally, DXA is the most commonly used for various reasons, including: emission of less radiation, availability, and lower cost. Another method that estimates the volume of fat and lean body mass is bioimpedance analysis (BIA).

SUMMARY

In one aspect, the technology relates to a method including: receiving a first signal corresponding to a measurement of a patient biological condition; receiving a second signal corresponding to a measurement of a patient performance condition; processing the first signal and the second signal; generating a visual representation of a diagnostic assessment, where the diagnostic assessment is based at least in part on the patient biological condition and the patient performance condition; and marking the visual representation with the measurement of the patient biological condition and the measurement of the patient performance condition. In an example, the visual representation comprises a two-axis plot, and wherein a first axis of the two-axis plot corresponds to the patient biological condition and a second axis of the two-axis plot corresponds to the patient performance condition. In another example, the method further includes accessing a data set; processing the data set; generating a curve based at least in part on the processed data set; and marking the visual representation with the curve. In yet another example, the data set comprises at least one of an age-matched population data set, a gender-matched population data set, and an ethnicity-matched population data set. In still another example, the data set is selected based on at least one of an age, a gender, and an ethnicity of the patient.

In another example of the above aspect, processing the first signal and the second signal comprises storing the measurement corresponding to the first signal and the measurement corresponding to the second signal in an historical database. In an example, processing the first signal and the second signal include indexing the measurement of the patient biological condition and the measurement of the patient performance condition against a matched data set. In another example, marking the visual representation comprises marking the visual representation with the indexed measurement of the patient biological condition and the indexed measurement of the patient performance condition. In yet another example, the method further includes marking the visual representation with an historical measurement of a patient biological condition and an historical measurement of a patient performance condition. In still another example, the method further includes displaying, simultaneously with the visual representation a rendering of a patient, wherein the rendering corresponds to the patient biological condition.

In another aspect, the technology relates to a method including: performing a dual energy x-ray absorptiometry scan of at least a portion of a patient using a dual-energy absorptiometry system to acquire a plurality of dual energy x-ray absorptiometry data; receiving a signal corresponding to a functional performance indicator of the patient; accessing from a computer database at least one population dataset; computer-processing the plurality of dual energy x-ray absorptiometry data and the signal corresponding to the functional performance indicator to obtain a comparison to the at least one population data set; and generating a visual representation of the comparison indexed against the at least one population data set. In an example, the computer-processing step comprises computer processing the plurality of dual energy x-ray absorptiometry data to determine an estimate of the patient's body composition. In another example, the computer-processing step comprises computer processing the plurality of dual energy x-ray absorptiometry data to determine an estimate of the patient's bone mineral density. In yet another example, the computer-processing step comprises computer processing the plurality of dual energy x-ray absorptiometry data to determine an estimate of the patient's muscle mass. In still another example, the computer-processing step comprises computer processing the plurality of dual energy x-ray absorptiometry data to determine an estimate of the patient's adipose tissue.

In another example of the above aspect, the received signal corresponds to a result of a short physical performance battery assessment of the patient. In an example, the received signal corresponds to a handgrip strength assessment of the patient. In another example, the received signal corresponds to a gait speed assessment of the patient. In yet another example, the received signal corresponds to a timed get up and go assessment of the patient. In still another example, the received signal corresponds to a standing balance assessment of the patient.

In another example of the above aspect, the received signal corresponds to a fall proclivity assessment of the patient. In an example, the accessing step comprises accessing at least one of an age matched population data set, a gender matched population data set, and an ethnicity matched population data set. In another example, the generating step comprises generating at least one of a printable report of the comparison indexed against the at least one population data set, a visual representation of the comparison indexed against the at least one population data set, a report depicting a colorized body composition map of the patient, and a report depicting asymmetrical muscle mass in a patient's limbs.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Non-limiting examples of various systems and methods utilized for imaging of bodies or parts thereof, and using the information gathered from said systems and methods for analysis, include:

U.S. patent application Ser. No. 14/553,533, filed Nov. 25, 2014, entitled "Bone Densitometer"

U.S. Pat. Nos. 6,081,582; 7,725,153; 8,792,689; and 9,179,873

U.S. Published Patent Application Nos. 2011/0235886 and 2010/0234719

WEAR, James et al., "CZT detector for dual energy x-ray absorptiometry (DEXA)", Proceedings of SPIE Vol. 4142, Penetrating Radiation Systems and Applications II, (Dec. 18, 2000), pages 175-188

LEHMANN, L. A. et al., "Generalized image combinations in dual KVP digital radiology", Medical Physics, Vol. 8, No. 5, September/October 1981, pages 659-667

SORENSON, James A. et al., "Simulation studies of dual-energy x-ray absorptiometry", Medical Physics, Vol. 16. No. 1, January/February 1989, pages 75-80

The disclosures of each of the above-identified patents and publications are hereby incorporated by reference herein in their entireties.

Pathologies and physiological conditions described in the present application are further described in the following:

LUSTGARTEN, M. S. et al., "Assessment of analytical methods used to measure changes in body composition in the elderly and recommendations for their use in Phase II clinical trials", J. Nutr. Health Aging, May 2011, 15(5): 368-375

SAYER, Avan Aihie et al., "New horizons in the pathogenesis, diagnosis and management of sarcopenia", Age and Ageing Jan. 11, 2013, 42: pages 145-150

The disclosures of each of the above-identified patents and publications are hereby incorporated by reference herein in their entireties.

Figure 1:
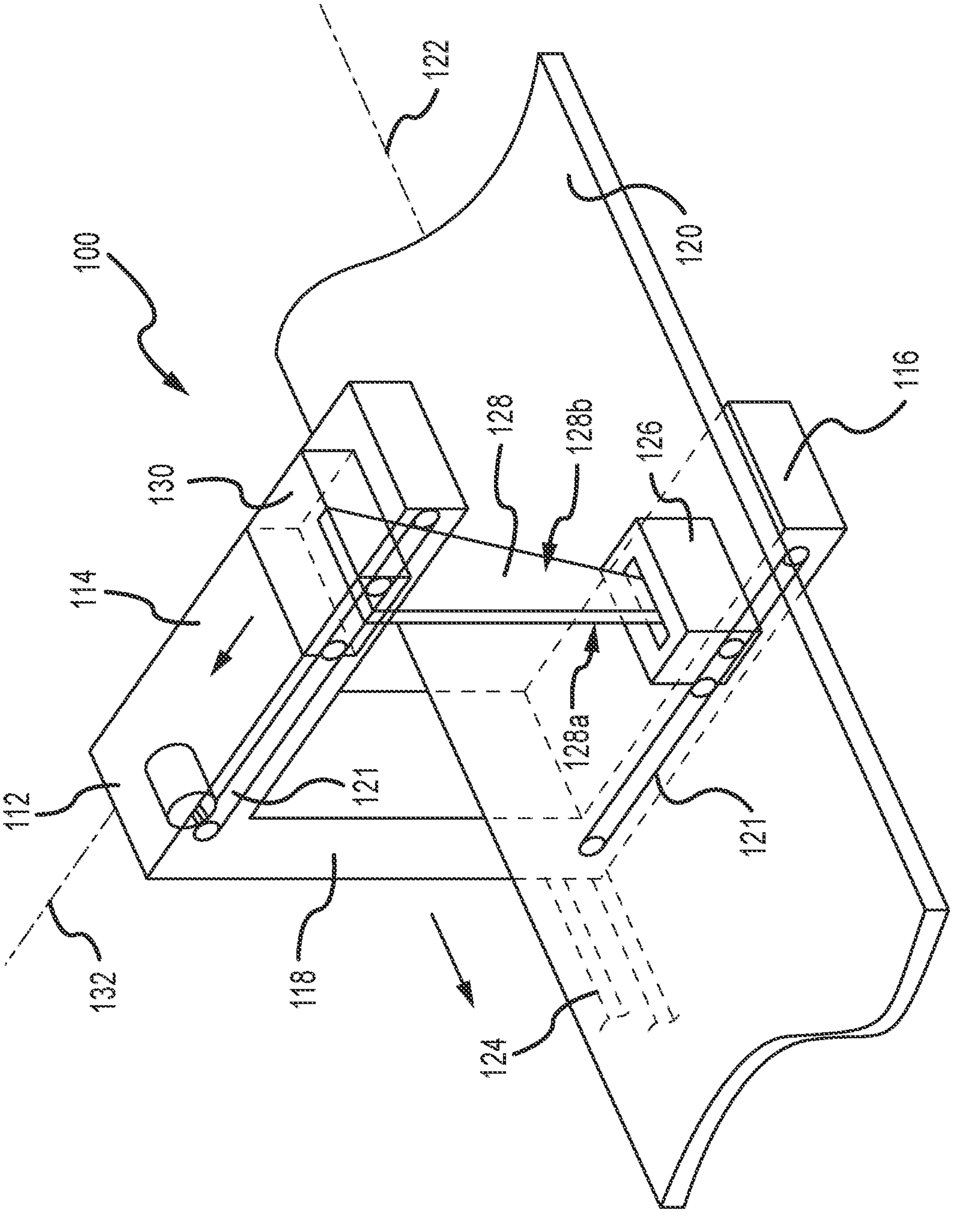
FIG. 1 depicts a perspective view of a transverse scanning densitometer in accordance with one embodiment of the technology.

FIG. 1 depicts a perspective view of a transverse scanning densitometer 100 in accordance with one embodiment of the technology. The densitometer 100 may also be referred to herein as a dual-energy x-ray absorptiometry (DXA) machine. The densitometer 110 includes a support arm 112 having vertically opposed horizontal arms 114 and 116 separated by vertical bar 118. A horizontal planar patient support table 120 is disposed between the horizontal arms 114, 116 and extends along a longitudinal axis 122. A belt drive system 124 of a type well known in the art, allows motion of the support arm 112 longitudinally along longitudinal axis 122 for the length of the table 120. In other embodiments, other types of drive systems, including racks and gears, may be utilized. The longitudinal axis 122 of the table 120 is generally substantially parallel to a longitudinal axis of a patient lying on the table 120.

An x-ray source 126 is within the lower arm 116. The x-ray source emits a collimated fan beam 128 of x-rays directed upward through the table 120. The beam 128 is detected or otherwise received by a linear detector 130. The fan beam 128 is oriented so that its narrowest extent 128*a* is along a transverse axis 132 and its widest extent is along the longitudinal axis 122. The table 120 is generally radiolucent so as to provide a support surface without significantly affecting the attenuation of the fan beam 128.

The x-ray source 126 and linear detector 130 may be moved transversely along the transverse axis 132. The x-ray source 126 and linear detector 130 are configured so as to move along the arms 114 and 116. This movement allows for transverse scans of the patient on the table 120. Motion of the x-ray source 126 and detector 130 is synchronized by belt-drive actuation mechanisms 121 as will be well understood to those of ordinary skill in the art. As with the belt drive system 124 described above, other types of drive mechanisms can be utilized in place of the belt-drive actuation mechanisms 124.

Figure 2:
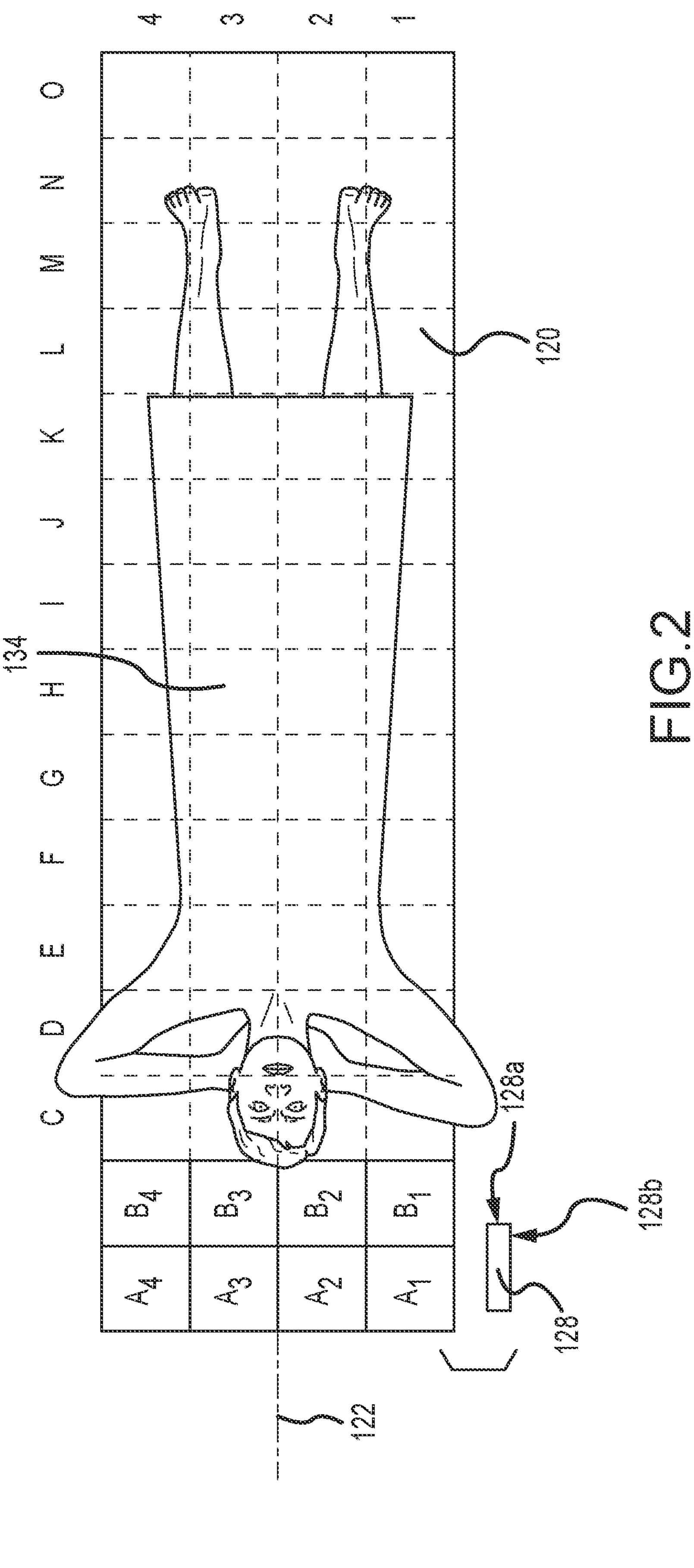
FIG. 2 depicts a top plan view of the table of the transverse scanning densitometer of FIG. 1.

FIG. 2 depicts a top plan view of the table 120 of the transverse scanning densitometer of FIG. 1. Certain of the components described above are not depicted in FIG. 2 for clarity. The fan beam 128 may be scanned over the surface of table 120 and hence may scan the whole body of patient 134 so as to generate a series of transversely extending scan images that may be merged into a single composite image or data set. Alternatively, a plurality of scan images can be merged into a single composite image for a particular body structure or part. For example, a first scan image may encompass, in sequence, areas A1, A2, A3, and A4. The x-ray source and linear detector, described above, may move transversely as required, emitting and receiving x-ray energy along the various sequential areas. At the end of this scan, motion of the support arm, described above, in the longitudinal direction may be performed. For example, the support arm may move towards the feet of the patient, so as to align with a second area of the patient such that the detector may perform a second scan image. The second scan image may be in order of areas B4, B3, B2, and B1. Alternatively, the arm may return to the side of the table 120 where it began the first image scan and scan areas B1, B2, B3, and B4. Because the transverse width of the patient 134 is substantially less than the superior to inferior height of the patient, each scan image, e.g., all of areas 1-4 in each of path A or path B, is acquired at a time closely proximate to its adjacent scan images and thus the risk of patient motion and the amount of patient motion may be substantially reduced. This is one of several marked advantages over imaging systems that that perform scans along the longitudinal axis of the patient.

In other embodiments, transverse scans of particular body parts may be performed. In one example, a complete transverse scan of the ribcage may include scans along scan paths E, F, G, and H. A transverse scan of a single body part that does not extend across an entire transverse scan path can also be performed. For example, the left femur may be scanned by imaging areas I1, I2, J2, J1, K1, and K2. Other transverse scan paths are contemplated.

The radiation source 126 may be a radioisotope or an x-ray tube running at constant voltage to produce a polyenergetic radiation beam. The beam may be subsequently filtered with a K-edge filter to form two energy modes. Alternatively, the radiation source 126 may be an x-ray tube run in a switched voltage mode where the voltage on the x-ray tube is periodically changed from a high to low voltage shifting the energy spectrum of the produced x-ray beam. Data is acquired by a broad band detector 130 and is sequentially high and low energy data as may be used in dual energy measurements. Other techniques including rotating filter wheels and the like may be used to produce sequential dual energy beams. The detector 130 may also include detection elements for detecting high energy radiation and detection elements for detecting low energy radiation. A user interface include a display and other input/output options, such as those discussed below with reference to FIGS. 8-9, may be operatively coupled to the densitometer 100 for displaying results or other information gathered or generated by the densitometer, as discussed herein. For instance, the user interface may be operatively coupled through a network or wired connection to the densitometer 100.

Figure 3:
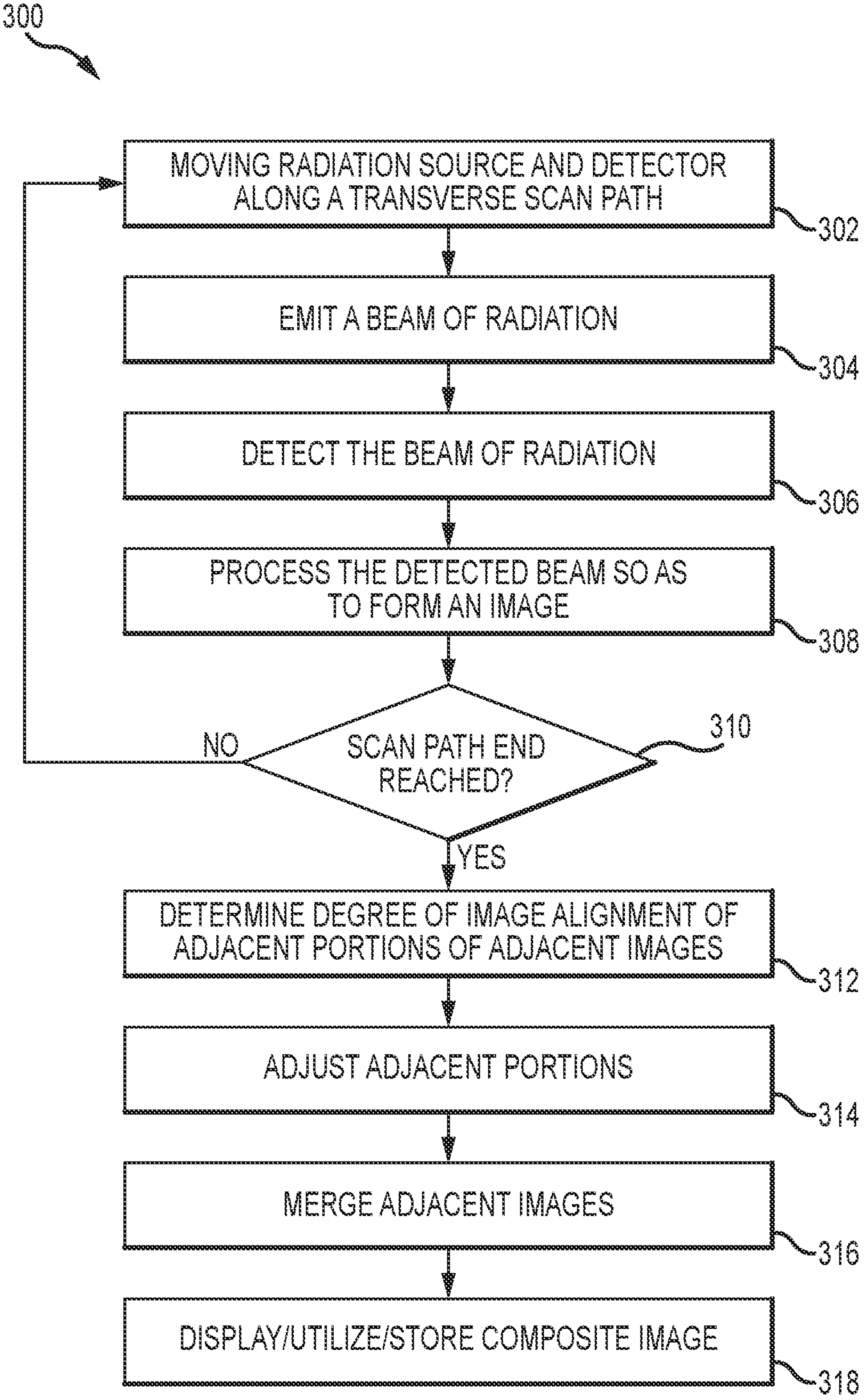
FIG. 3 depicts a method of generating images during a transverse scanning procedure in accordance with an embodiment of the technology.

FIG. 3 depicts a method 300 of generating images during a transverse scanning procedure in accordance with an embodiment of the technology. The method 300 provides for a scanning densitometer having a radiation source collimated to produce or emit a beam of radiation directed across a patient to an electronic radiation detector, the latter of which receives, detects, or otherwise measures the beam of radiation passing through the patient. A scanning assembly moves the radiation source and radiation detector along at least one scan path transverse to a longitudinal axis of a patient, operation 302. While moving, the radiation source emits the beam of radiation, operation 304, which is detected by the radiation detector, operation 306. The detected beam is then processed so as to form an image, operation 308. Since the beam has a predefined width, the size of each image is based on the beam width and a length of travel of the scanning assembly. Any number of discrete images may be formed as the scanning assembly travels along the transverse scan path. As the scanning assembly traverses the scan path, one or more sensors determine a position thereof. If the end of the scan path is not reached as depicted in operation 310, flow branches to NO and movement of the scanning assembly (as well as operations 302-308) continue, thus generating a plurality of images along the scan path. Once the end of the scan path is reached at operation 410, flow branches YES, where a degree of image alignment is then determined at operation 312.

In certain embodiments, the image alignment of adjacent portions of adjacent images is determined. The size of the adjacent portions may be determined based on, e.g., number of pixels in the image, a percentage of the total area of the image, or other factors. These adjacent portions of the adjacent images may be adjusted, operation 314, so as to allow different degrees of overlap to better match structures within the images having various heights within the patient. The degree of image alignment may evaluate only the bone portion of the image, only a lean tissue portion of the image, only a fat tissue portion of the image, or a combination of any of the three. The method 400 may improve the ability to match the images by eliminating structure such as soft tissue whose matching is not critical. In other embodiments, determining the degree of image alignment may include determining a structure height based on a known divergence of the radiation beams and the determined overlap, thus improving image alignment. The height may be used to scale each scan image prior to merging adjacent scan images. Thus, the system and method described herein may employ the difference in overlap between adjacent scan images to correct the magnification of the image. Thereafter, the adjacent images are merged at overlapping areas, operation 316, to form a composite image that includes all of the combined adjacent images. Prior to merging, the images may be weighted so as to eliminate any disproportionate influence of redundant data in the images. Regardless, the proposed technologies do not rely on weighting alone, as such methods may produce a blurring of the merged image. Blurring of the image may be reduced or eliminated by correcting overlap of the images, as described herein. This composite image has an overlap corresponding to a best matching of the plurality of scan images. In operation 318, the composite image may then be stored, displayed, and/or otherwise utilized for marking and analysis of tissue, as described herein.

The patient support may support a supine patient with the patient's head and feet lying along a longitudinal axis and the scanning assembly may move the radiation source and electronic detector along a series of transverse scan paths substantially perpendicular to the longitudinal axis across the patient to acquire the scan images. Such a method includes operations similar those depicted in FIG. 3. As the end of a scan path is reached, the system may then traverse a second transverse scan path that is substantially parallel to the first transverse scan path. Images obtained along the second transverse scanned path are processed as described in FIG. 3, operations 312-316. However, degree of image alignment may be determined for both of adjacent images in the same scan path, as well as adjacent images in adjacent scan paths. Such processing can produce a master composite image that includes all images in all scan paths, which may then be utilized as described herein.

Images obtained from various imaging systems, such as those referred to herein, can divide the body into three components: fat tissue, lean ("lipid-free soft tissue") tissue, and bone mineral content ("BMC"). Systems that emit dual energies during an imaging or scanning sequence may generally be utilized to identify a maximum of two of those components at a time. For example, in areas of the body where bone is primarily located, BMC may be identified as described generally herein. In areas without bone, fat tissue and lean may be identified. Similarly, in primary fat regions that are substantially without lean tissue, such as subcutaneous fat regions, fat tissue and non-fat material can be identified. In those primary fat regions, the non-fat material is principally composed of water.

Figure 4:
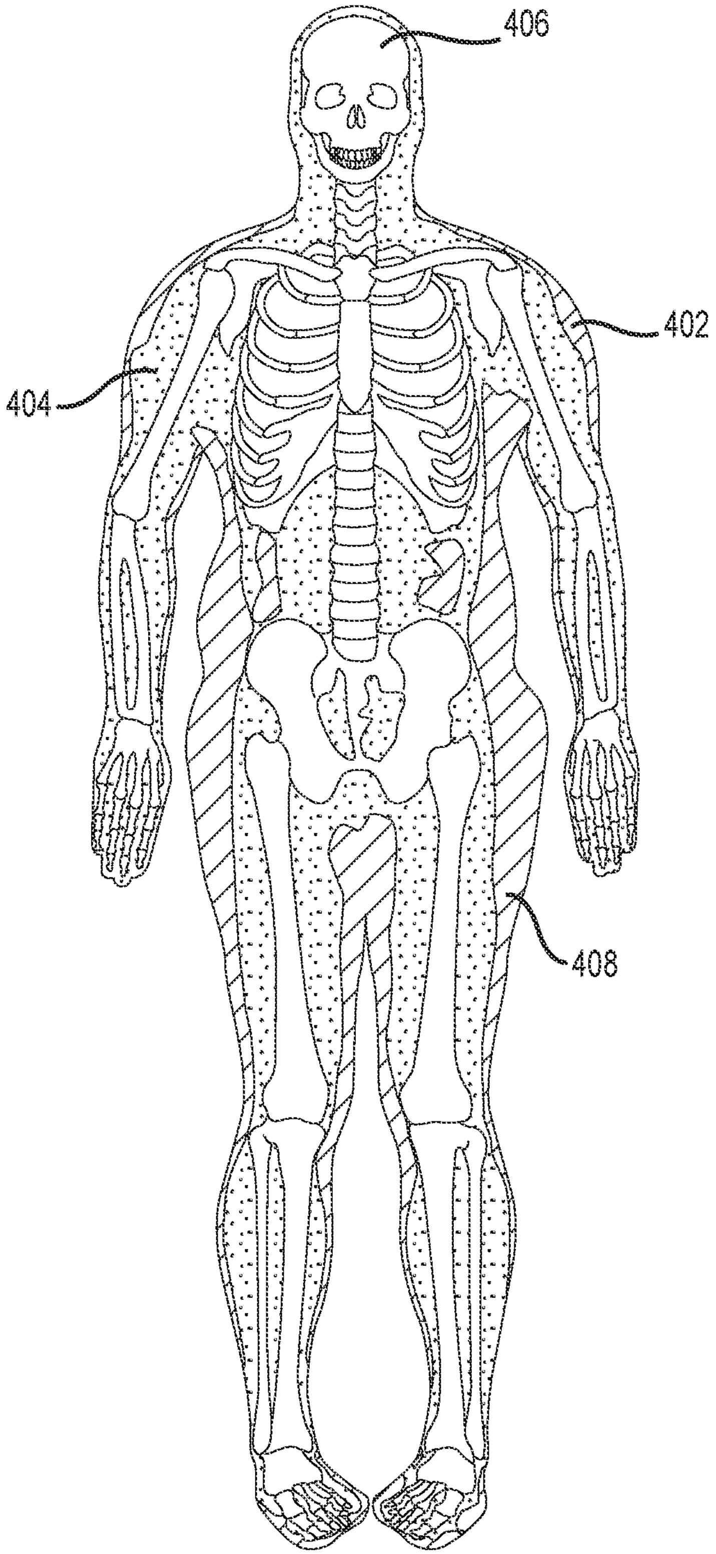
FIG. 4 depicts an image from a scan of a relatively fit, but overweight young male depicting tissue components therein.
Figure 5:
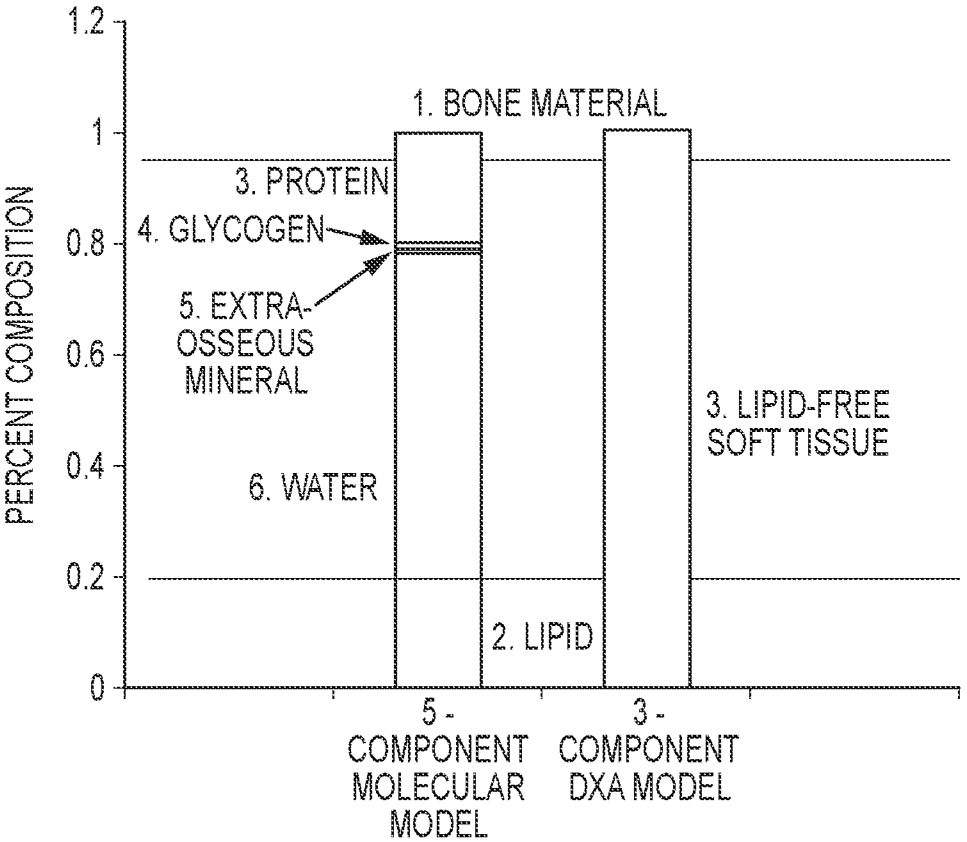
FIG. 5 depicts a five component molecular model of body composition compared to a three component molecular model.

As an example, FIG. 4 depicts a scan of a relatively fit, but overweight young male depicting such components therein. The different stippling and hashed lines identify fat tissue (hash lines, 402), lean tissue (stippling, 404), and BMC (white, 406). A sample colored version of such a similar scan can be found in Carla M. M. Prado, Steven B. Heymsfield, *Lean Tissue Imaging: A New Era for Nutritional Assessment and Intervention*, JPEN J Parenter Enteral Nutr. 2014; 38(8):940-953, the disclosure of which is incorporated by reference herein in its entirety. Simplifying a human body into three components or categories, however, is an imperfect approximation as the human body is complex. Such an approximation is helpful, however, in making some determinations, such as relative locations of lean tissue and bones, bone densities, and so on. The approximation does have limitations, however, in using the above referenced systems to identify other physiological conditions or properly determine tissue amounts in patients having those physiological conditions. For instance, FIG. 5 shows some of the complexities and potential errors in approximating tissue types into only three categories. Additional information regarding FIG. 5 can be found in IAEA Human Health Series No. 15 "Dual Energy X-ray for bone density and body composition assessment" found at www.iaca.org/Publications/index.html, the disclosure of which is hereby incorporated by reference herein in its entirety.

In approximating an amount of lean tissue, it is useful to understand that lean tissue is composed primarily of water. In a patient with a fairly stable level of hydration, the lean tissue determination discussed above works reasonably well as a surrogate for muscle mass. Various pathological conditions and situations, however, cause the lean tissue determination to no longer be a good surrogate for muscle mass. For example, edema in appendages of the patient, such as the legs and arms, may cause a significant divergence from lean tissue determinations and muscle mass locally in the appendage. When analyses or treatments of other ailments rely on the lean tissue determination, those analyses will similarly be inaccurate due to the error. For instance, the error is particularly an issue in the diagnosis of sarcopenia, which is a degenerative loss of skeletal muscle mass, quality, and strength. Sarcopenia is a component of the frailty syndrome and is associated with aging and other pathologies. Proper diagnosis of sarcopenia depends on an accurate measurement of appendicular muscle mass in aged persons. This same population, however, can commonly have edema, thus confounding the measurements obtained by imaging systems such as those referenced and described herein.

The technologies further described herein allow for a more accurate measurement of muscle mass, including in the legs and arms, even in the presence of edema. Within the body, areas that are primarily fat tissue without overlapping muscle tissue can be analyzed using the dual energy radiation techniques above to identify an amount of fat tissue and an amount of water, potentially representative of edema. In most individuals, the body has a layer of nearly pure fat cells just under the skin, termed "subcutaneous fat." In the projected image of FIG. 4, the subcutaneous fat portion 408 is substantially free of muscle. The subcutaneous fat is often a good primary fat target for analysis. The amount of water or degree of edema is determined based on an analysis of the primary fat target, and that determination is used to correct a lean tissue measurement for edema or water content. Of note, fat cells in fat tissue are not 100% lipid because they contain water and other non-lipid components.

In an example, a correction for the presence of edema may be obtained by determining an amount or percentage of fat in the subcutaneous fat layer in an appendage of the patient, such as an arm or a leg. The amount of fat or percentage of fat determination is compared to a predetermined or predefined standard. Such standards may be, for example, the expected fat percentage or amount of fat of the subcutaneous fat from an individual known to not have edema, or the fat percentage or fat amount measured in another part of the body of the same patient, such as the subcutaneous fat of the abdominal area. The standard amount of fat or fat percentage standard is referred to herein as the "reference amount".

Based on the comparison of the fat amount or fat percentage for the particular patient to the reference amount, a correction for edema or other physiological conditions may be made to the lean component of the measurement in the appendage from which the primary fat target was located. For example, lean mass for a particular appendage could be corrected based on the difference of the measured fat percentage of the patient's subcutaneous tissue to the reference amount percentage of fat. In some examples, the correction is a multiplicative factor times the lean mass of the limbs based on a functional relationship between the measured fat percentage and the reference amount fat percentage. For instance, the following equation provides one example for correcting a lean tissue determination:

$$L_C = f(F_p, F_S) \times L_E \quad (1)$$

where:

- $L_C$ is the corrected lean tissue amount;
- $F_p$ is the fat amount or fat percentage for the primary fat target of the patient;
- $F_S$ is the standard amount of fat or the standard fat percentage; and
- $L_E$ is the estimated lean tissue amount prior to correction.

The corrected lean tissue amount may also be referred to herein as muscle mass. In a particular embodiment, the equation used to correct the estimated lean mass amount is as follows:

$$L_C = \frac{F_p}{F_S} \times L_E \quad (2)$$

Other equations and relationships to correct the estimated lean tissue amount are also contemplated.

FIG. 6 depicts a method 600 for determining muscle mass of a patient by correcting an estimated lean mass. At operation 602, radiation emitted from a densitometer or dual-energy radiation device is detected. For instance, the radiation may be a beam that has passed through a patient and is detected by a detector, such as linear detector 130 as described above. Generally, imaging systems can measure fat percentage and total mass, or fat and lean mass, on a pixel-by-pixel basis, but other area measurements, such as square centimeters, may also be utilized. Based on the detected radiation emission, a scan representation is generated at operation 604. The scan representation may be for a particular region of interest of the patient, such as appendage like an arm or a leg or portions of an arm or leg. For example, because edema is normally present in the lower appendages, the area of interest may be the portion of the leg below the knee. The scan representation may also be of the whole body of the patient, similar to the scan representation in FIG. 4. In some examples, the scan representation may not be an image, but another type of representation, such as a chart, graph, or other model.

At operation 606, a primary fat target is identified in the scan representation. The primary fat target may be any portion of the body that is predominately not occupied by muscle. For example, as discussed above, a subcutaneous fat region of the patient is a suitable primary fat target. Identifying the primary fat target may also include identifying at least one pixel in the scan representation that is representative of the primary fat region. For example, in the scan representation depicted in FIG. 4, the primary fat target may be the subcutaneous fat region 408, as identified in the figure. Each pixel forming the representation of the subcutaneous fat region may be identified in operation 606, or a subset of those pixels may be determined. At operation 608, the primary fat target may be modeled to determine a mass, volume, or other characteristic of the primary fat target. Additionally, a total water or lean tissue level of the primary fat target may be determined as part of operation 608. Of note, the lean tissue within the primary fat target is predominately water rather than muscle. The primary fat target may be modeled by determining a depth or average depth of the primary fat target from the scan representation. Alternatively or additionally, the depth of fat may be extrapolated so as to generate a substantially annular volume of the primary fat target (e.g. 360° around the appendage). Other detailed examples of modeling visceral fat are provided in U.S. Pat. No. 7,725,153 and U.S. Patent Publications 2010/0234,719 and US 2011/0235,886, the disclosures of which are hereby incorporated by reference herein in their entireties.

Figure 6A:
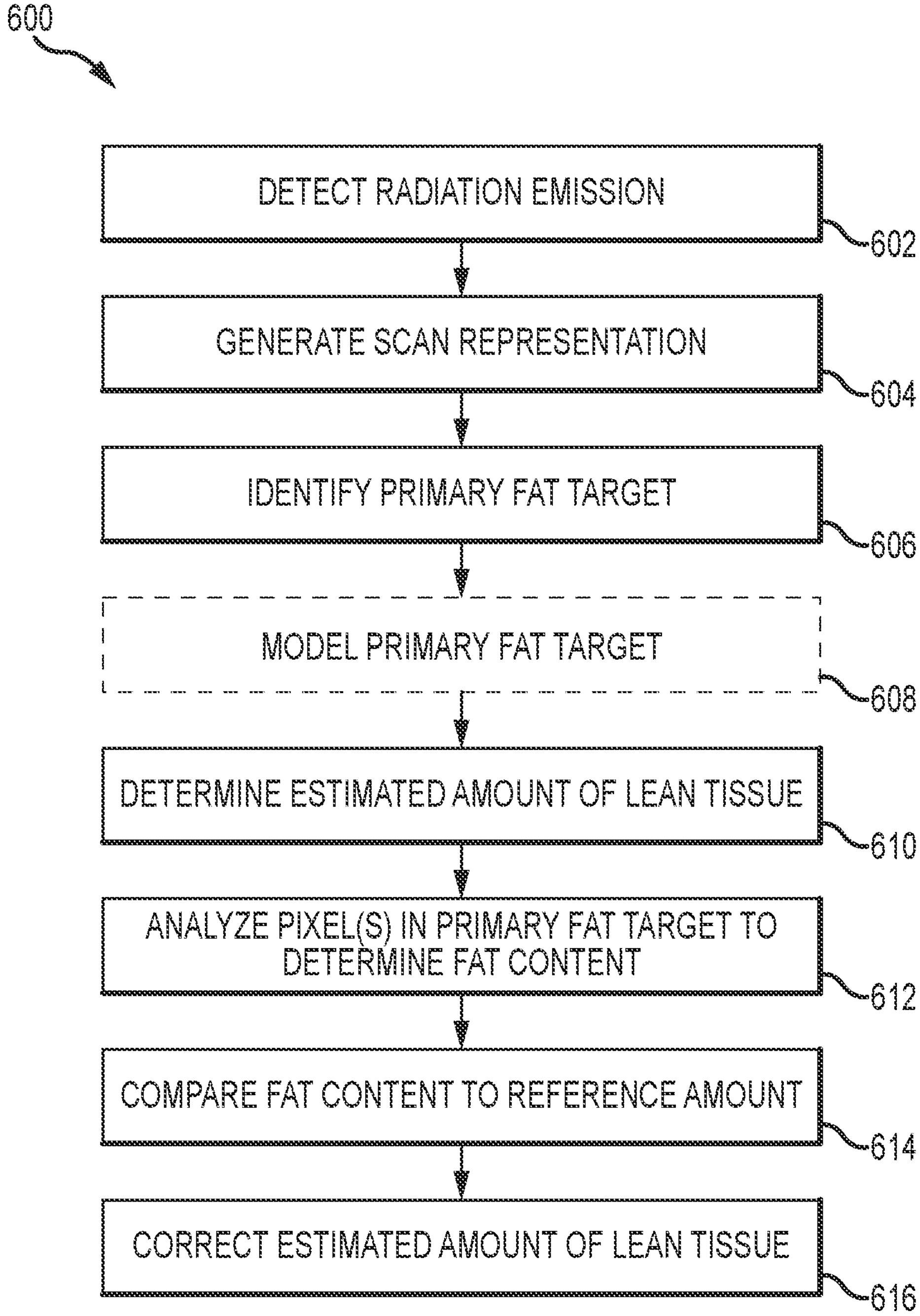
FIG. 6A depicts a method of correcting for physiological condition such as edema.
Figure 6B:
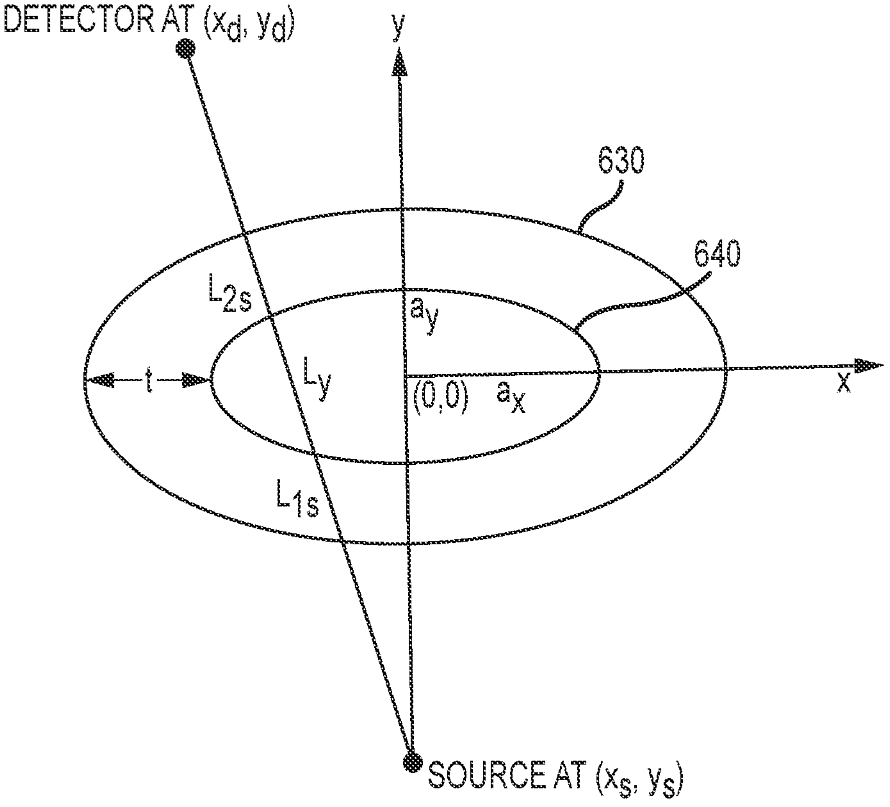
FIG. 6B depicts a geometrical model for modeling a primary fat target.

As an example, FIG. 6B illustrates geometry related to modeling a primary fat target. The outline of the region of interest is approximated by an ellipse 630 and the inner outline of the primary fat target is approximated by a concentric inner ellipse 640. The primary fat target is between the two ellipses. As discussed above, where the subcutaneous fat region is the subcutaneous fat region of an appendage, it generally wraps around the appendage, similar to an ellipse. Let ray i be the line connecting source point $(x_s, y_s)$ of a fan beam of x-rays to detector point $(x_d, y_d)$. The total length of intersection of the line with the concentric ellipses is given by $$L = L_{1s} + L_{2s} + L_v \quad (3)$$

Where $L_{1s}+L_{2s}=L_s$, the total length of the line i through subcutaneous fat, and $L_v$ is the length of the same line i through the tissue surrounded by the subcutaneous fat. The pertinent line lengths can be calculated or estimated as discussed below, or in some other way based on known parameters such as the positions of the source and detector relative to ellipses 630 and 640.

The fat percentage (% $Fat_{vi}$) in the central region for the raypath that is along line i and is from the source focal spot to a detector position that corresponds to a dual energy x-ray measurement for a pixel in the image will be $$\%\ \text{Fat}_{vi} = (\text{total}\ \%\ \text{fat})_i L_v / L \quad (4)$$

The quantity (total % Fat)$_i$ for use in Equation 4 is estimated from the dual energy x-ray measurements for the raypath using known DXA processing.

Figure 6C:
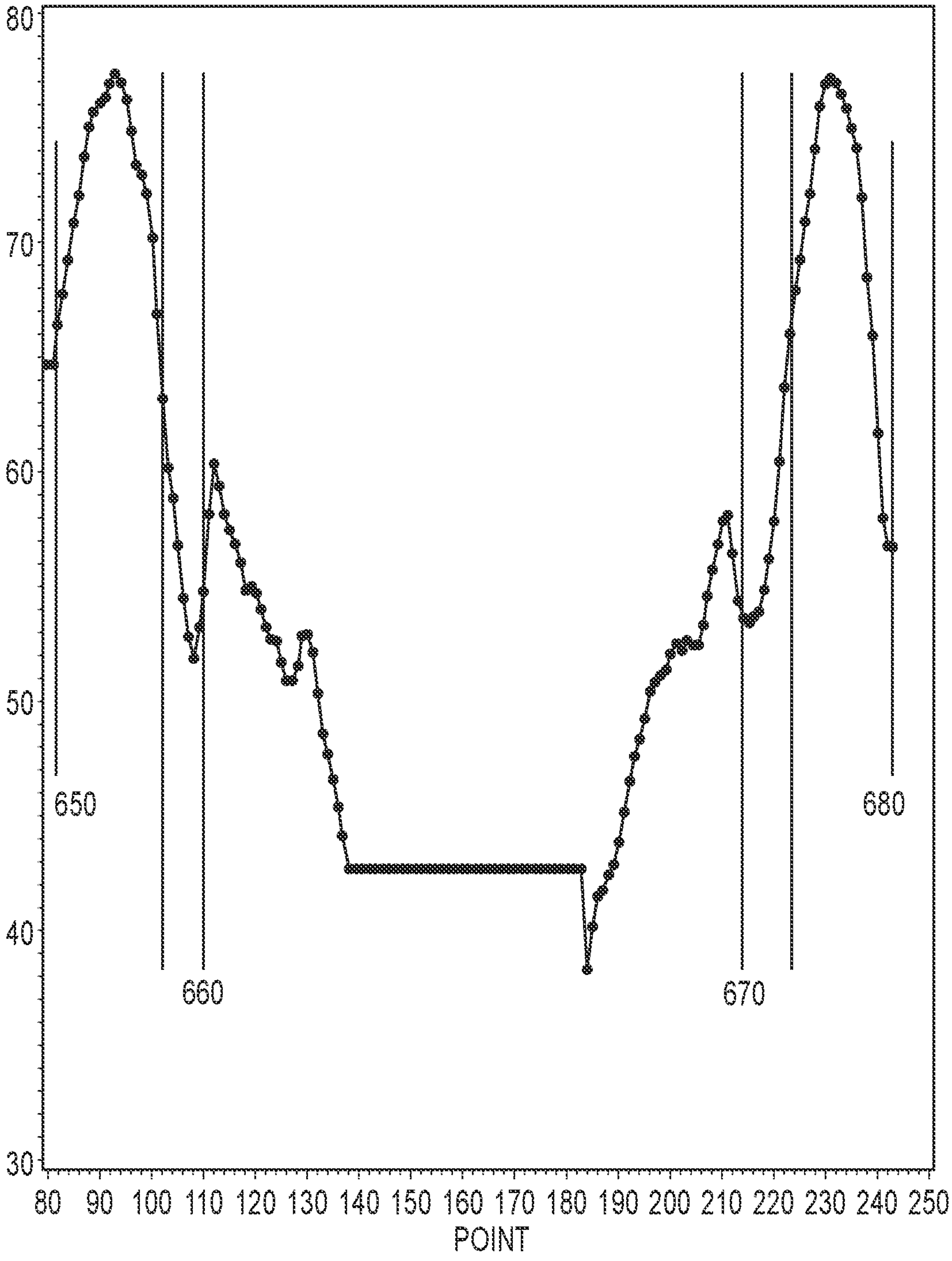
FIG. 6C depicts a plot of fat percentage by pixel.

The inner ellipse 52 may be defined by the major axes ax and ay and the outer ellipse defined by $b_x$ and $b_y$. The parameters can then be estimated from a profile plot of the fat percentage vs. pixel number as illustrated in FIG. 6C, with any needed accounting for geometric factors related to using a fan beam of x-rays. The total lengths of the subcutaneous fat regions ($L_{1s}$, $L_{2s}$) may be calculated based on:

$$L_{1s} + L_{2s} = L - \sqrt{(x_2 - x_1)^2 + (y_2 - y_1)^2} \tag{5}$$

The equation may be solved using a number of mathematical techniques, including those discussed in U.S. Pat. No. 7,725,153. For example, the following sets of equations representing the right-hand side of the Equation 5 can be used to solve for the lengths based on data in a plot such as the one in FIG. 6C.

$$\begin{cases} x_2 = x_s + t_2 d_s \\ y_2 = y_s + t_2 d_y \\ x_1 = x_s + t_1 d_x \\ y_1 = y_s + t_1 d_y \end{cases} \quad \text{Eq. Set 6}$$

$$\begin{cases} t_1 = \left(-R + \sqrt{P}\right)\big/F \\ t_2 = \left(-R - \sqrt{P}\right)\big/F \end{cases} \quad \text{Eq. Set. 7}$$

$$\begin{cases} P = R^2 + F - FG \\ R = d'_x x'_s + d'_y y'_s \\ F = (d'_x)^2 + \left(d'_y\right)^2 \\ G = (x'_s)^2 + (y'_s)^2 \end{cases} \quad \text{Eq. Set. 8}$$

$$\begin{cases} x'_s = \dfrac{x_s}{a_x} \\ y'_s = \dfrac{y_s}{a_y} \\ d'_x = \dfrac{d_x}{a_x} \\ d' = \dfrac{d_y}{a_y} \\ d_x = x_d - x_s \\ d_y = y_d - y_s \end{cases} \quad \text{Eq. Set. 9}$$

In addition the width of the anterior and posterior sections of a subcutaneous fat region may be determined by analyzing the representative scan, such as the one shown in FIG. 4, as discussed below. Such widths could then be used to approximate the ellipse shown in FIG. 6B through various mathematical techniques.

FIG. 6C illustrates a fat percentage estimated from DXA measurements for pixel positions in a DXA image. The horizontal axis is the pixel number in the DXA image across the width of a region of interest of the patient. The vertical axis is the fat percentage. The vertical axis represents the total fat percentage for the respective pixel positions, and thus typically includes the entire region of interest, such as an appendage. For instance, it is the percentage of fat in the tissue that is along the x-ray beam path from the source to the x-ray detector element(s) that corresponds to a pixel in the image. The shoulders of the curve between 650 and 660 and 670 and 680 represent a subcutaneous fat region for the patient. Where the pixel width is known, the width of the subcutaneous region may be determined. In addition, the percentage of lean tissue for the subcutaneous region may also be determined from the plot in FIG. 6C by subtracted from the displayed fat percentage as the subcutaneous fat region should only include fat tissue and lean tissue.

Returning to FIG. 6A, at operation 610, an estimated amount of lean tissue is determined. The estimated amount of the lean tissue may also be based in part on the primary fat target model generated in operation 608.

As an example, the width of the primary fat target, such as the subcutaneous fat region, is determined at each height (H) of the limb on the posterior (p) and anterior (a) sides of the limb from the far extremity, such as toes or fingers or a foot or a hand, to the trunk. For example, for a leg, the width of the subcutaneous fat region changes between the ankle, the hip, or the knee. As such, measurements or estimates of the width of the fat layer may be taken at different heights to more accurately predict the shape and overall size of the subcutaneous fat region. The width of the subcutaneous fat region on the posterior side for a particular level may be represented as $w_s^p(H)$, and the width of the subcutaneous fat region on the posterior side for a particular level may be represented as $w_s^a(H)$. In some embodiments, the width of the limb ($w_l(H)$) at a particular level is measured from the image. In such embodiments, the width of the skeletal muscle ($w_m(H)$) at each level may be estimated by the following equation:

$$w_m(H) = w_1(L) - [w_s^p(H) + w_s^a(H)] \tag{10}$$

The lean tissue of the skeletal muscle at level L is can be estimated with a DXA machine by analyzing the pixels representing the skeletal muscle. By including only the skeletal muscle pixels in determining the lean mass, the lean mass estimation is more likely to be representative of muscle mass.

Additionally, the fat mass of the limb at a given level may be approximated by an annulus of an ellipse, as a DXA machine is capable of measuring thickness (t) and widths with substantial accuracy. Based on the determined or measured widths or thicknesses, the subcutaneous fat can be modeled as a ring of fat encompassing the skeletal muscle.

In another example, determining an estimated amount of lean tissue may include removing the modeled primary fat target prior to analyzing the scan representation to determine an estimated amount of lean tissue. For instance, due to the subcutaneous fat wrapping around the skeletal muscle, the lean tissue (primarily water) may be included in the total lean mass estimation because the radiation passes through the whole region of interest. Accordingly, removing the modeled subcutaneous fat region from the analysis improves the estimation of muscle mass. Similarly, determining an estimated amount of lean tissue may also include removing the amount of water or lean tissue determined to be in the primary fat target, as that water or lean tissue may otherwise be inadvertently included in the lean mass determination and eventually in an estimation of muscle mass.

At operation 610, pixels of the primary fat target are analyzed to determine fat content within the primary fat target. In some embodiments, a single pixel within the primary fat target portion of scan representation may be analyzed to determine an amount of fat or a fat percentage for that pixel. In other embodiments, additional pixels representative of the primary fat target are also analyzed to determine an amount of fat or a fat percentage for those pixels. In such embodiments, the fat amount for each pixel may be summed and/or the fat percentages for the pixels may be averaged to determine an overall fat percentage for the primary fat target.

Once a fat amount or fat percentage for the primary fat target has been determined, that fat amount or fat percentage is compared to a reference amount at operation 614. As discussed above, the reference amount may be determined from a sample of patients not having edema. The reference amount may also be from another portion of the patient where edema is known to not be present. For example, in many elderly patients, subcutaneous fat may be located about the torso or midsection of the patient, while the appendages lack subcutaneous fat. Under such circumstances, the primary fat target may be proximate the torso and compared to reference amounts obtained from the appendages. Other reference amounts may be determined so as to represent a relatively healthy individual without edema. The reference amount may also be from a previous scan of the patient when it was known that the patient did not have edema.

Based on the comparison in operation 614, the estimated amount of lean tissue is corrected in operation 616. By correcting the estimated amount of lean tissue, a more accurate representation of the muscle mass for the patient is generated. The correction to the estimated amount of lean tissue may be accomplished by using equations (1) or (2) discussed above, or variations thereof. Other suitable correction factors based on the comparison in operation 614 are also contemplated. For instance, the lean tissue estimation may be corrected based on the following equation:

$$(w_s^p(L) + w_s^a(L)) \times w_m(L) \times E \tag{11}$$

where E is an edema correction derived by comparing a fat percentage of the primary fat target to a reference amount, such as a value derived by measuring a population of persons known not to have edema or a value obtained by measuring fat somewhere else on the person which has no edema or at least much less edema than the appendage being measured.

In some embodiments, the comparison operation 614 may not be performed, and a correction to the lean mass estimation may be made without reliance on such a comparison. For example, a correction for the hydration of the fat mass ($E_f$) and a correction of the hydration of the lean mass ($E_l$) may be utilized. The correction values $E_f$ and $E_l$ are derived from a determination of the fat percentage or fat amount of the primary fat target. The muscle mass (MM) may be determined according to the following equation:

$$MM = M_1 - M_f E'_f \tag{12}$$

where $M_l$ is the estimated lean mass, $M_f$ is the estimated fat mass as determined by the DXA machine, and $E'_f$ is a percentage of lean mass in the primary fat target. In some embodiments, a correction of the hydration of the lean mass ($E_l$) may be utilized. The following equation is representative of such an embodiment:

$$MM = E_1(M_1 - M_f E'_f) = M_l E_l - M_f E_f \tag{13}$$

In embodiments, the correction for the hydration of the fat mass ($E_f$) and the correction of the hydration of the lean mass ($E_l$) may be proportional to one another. In embodiments where the hydration of the fat mass is similar to the hydration of the muscle mass, both $E_f$ and $E_l$ may be represented by $E'_f$. In such embodiments, the muscle mass may be determined by the following equation:

$$MM = M_l E'_f - M_f (E'_f)^2 \tag{14}$$

Figure 7:
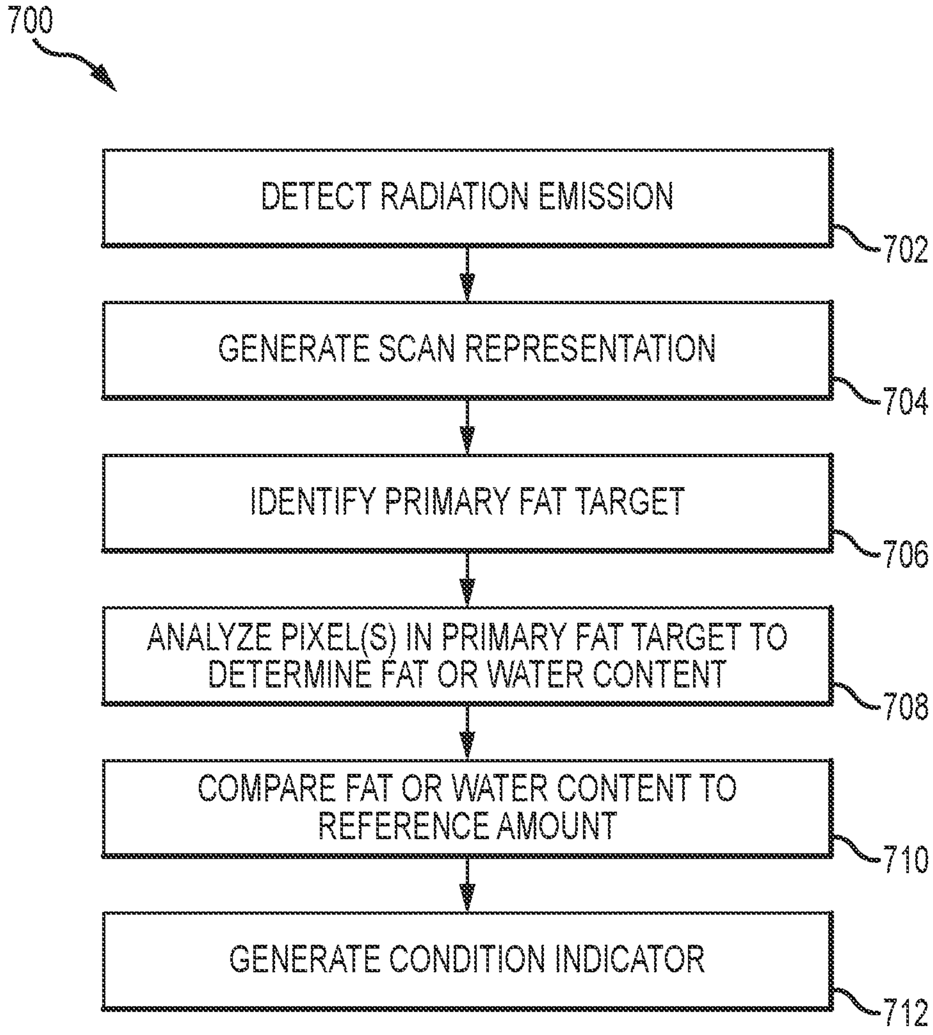
FIG. 7 depicts a method of identifying a physiological condition such as edema.

FIG. 7 depicts a method of identifying a physiological condition (e.g., edema). At operation 702, radiation emitted from a densitometer or dual-energy radiation device is detected. For instance, the radiation may be a beam that has passed through a patient a detected by a detector, such as linear detector 130 as described above. Generally, imaging systems can measure fat percentage and total mass, or fat and lean mass, on a pixel-by-pixel basis, but other area measurements, such as square centimeters, may also be utilized. Based on detected radiation emission, a scan representation is generated at operation 704. The scan representation may be for a particular region of interest of the patient, such as appendage like an arm or a leg. The scan representation may also be of the whole body of the patient, similar to the scan representation in FIG. 4. In some embodiments, the scan representation may not be an image, but another type of representation, such as a chart, graph, or other model.

At operation 706, a primary fat target is identified in the scan representation. The primary fat target may be any portion of the body that is predominately not occupied by muscle. For example, as discussed above, a subcutaneous fat region of the patient is a suitable primary fat target. Identifying the primary fat target may also include identifying at least one pixel in the scan representation that is representative of the primary fat region. For example, in the scan representation depicted in FIG. 4, the primary fat target may be the subcutaneous fat region as identified in the figure. Each pixel forming the representation of the subcutaneous fat region may be identified in operation 706, or a subset of those pixels may be identified.

At operation 708, pixels of the primary fat target are analyzed to determine fat content or water content within the primary fat target. The fat content may be a fat amount or a fat percentage. The water content may be a water amount or a water percentage. In some embodiments, a single pixel within the primary fat target portion of scan representation may be analyzed to determine a fat content or a water content for that pixel. In other embodiments, additional pixels representative of the primary fat target are also analyzed to determine a fat content or water content for those pixels. In such embodiments, the fat content or water content for each pixel may be summed and/or the fat percentages for the pixels may be averaged to determine an overall fat percentage for the primary fat target.

The fat content or water content determined in operation 708 is then compared to a reference amount at operation 710. As discussed above, the reference amount may be determined from a sample of patients not having the physiological condition. The reference amount may also be from another portion of the patient known not to display the condition (e.g., as described above in regard to subcutaneous fat in the torso area, but not appendages). Other reference amounts may be determined so as to represent a relatively healthy individual without the physiological condition. The reference amount may also be from a previous scan of the patient when it was known that the patient did not have the physiological condition.

Based on the results of the comparison, a condition indicator is generated at operation 712. The condition indicator indicates whether the patient has the physiological condition being tested. For example, if the results of the comparison at operation 710 reveal that the fat content in the primary fat target is below the reference fat amount, a condition indicator may be generated indicating that the patient has edema. In some embodiments, the fat content must be a certain amount below the reference fat amount before a condition indicator indicating edema will be generated. For instance, the edema condition indicator may only be generated if the fat content is a standard deviation below the reference fat amount. Where the primary fat target is being tested for only a region of interest, the condition indicator indicates that the patient has localized edema in the region of interest. Similarly, if the water content is above the reference water amount, a condition indicator may be generated indicating that the patient has edema. In some embodiments, the water content must be a certain amount above the reference water amount before a condition indicator indicating edema will be generated. For instance, the edema condition indicator may only be generated if the fat content is a standard deviation above the reference water amount. The condition indicator may be a screen item in a user interface or other indicator suitable to convey the physiological condition of the patient.

As discussed above, the method 600 and the method 700 may be performed for a region of interest or for the whole body of the patient. In embodiments where the methods are performed for the region of interest, the primary fat target and the pertinent lean tissue are located within the same region of interest, such as an arm of the patient. In embodiments where the methods are performed for the whole body, the primary fat target and the pertinent lean tissue may be located in any portion of the body. In some patients, however, the patient may not have a suitable primary fat target in the region of interest. For example, elderly patients may have minimal to no subcutaneous fat in their legs. For such patients, the primary fat target may be the subcutaneous fat of the abdomen, and the results obtained from analysis of the abdominal fat may be used to correct an estimated lean tissue amount in a separate region of interest, such as the leg, as described above.

Other techniques to correct lean mass estimations for edema may be based on the shape of the soft tissue versus, for example, the expected shape of the same tissue. That is, a limb where edema is present will look swollen, as compared to a limb where edema is not present. Bone landmarks may also be used as a basis for correction. For example, the position of knee relative to the outer contours of the leg may indicate the presence of edema as well.

Other techniques for correcting for the presence of edema include measuring the soft tissue area around the ankles, outside of the bone. This measurement may then be compared to the shape of the thigh, to detect and correct for swelling due to edema. In other techniques, multi-frequency bioelectric impedance may be used to measure the water content of the legs and/or arms, and use that to make an edema correction. Still another technique utilizes "water dilution," which can very accurately measure total body water, so as to perform an overall hydration correction to the lean mass. In water dilution, a patient drinks a known quantity of deuterated water, and after a suitable time for this to disperse through the body, a saliva sample is taken and the percentage of deuterated water of the saliva sample, along with the patient's mass, can be used to measure total water hydration.

The present technologies provide systems and methods for identifying, diagnosing, and presenting medical conditions to a clinician or patient. The types of conditions can be complex conditions that may require both an objective measurement, as well as a functional or performance-based measurement. In other examples, multiple objective measurements may be utilized for a diagnosis, and/or multiple functional measurements. As used herein, the term "measurements" refers to a measurement, observation, or data related to a patient.

"Objective measurements" are measurements that generally cannot be influenced by a patient or that do not require an action by the patient. These may include, but not be limited to: body weight, lean mass, bone density, blood cholesterol level, and so on. Objective measurements can be made by instruments, machines, devices, or other systems that collect various types of data. For example, such measurements may be obtained from DXA, MRI, CT scans, BIA, scales, blood tests, and so on. Other objective measurements may be obtained via use of skin fold calipers, scales, hydrostatic weighing machines, blood testing instruments and equipment, or other instruments. Examples of equipment that may be used to obtain objective measurements, as well as the types of measurements themselves, as described above.

"Functional measurements" are defined as a measurement that requires the patient to perform an action. Functional measurements include, but are not limited to, grip strength assessments, gait speed or any gait abnormality assessments, leg press strength assessments, standing balance assessments, timed get up and go assessments, fall proclivity assessments, and short physical performance battery (SPPB) tests. SPPB tests include a combination of gait speed, standing balance, and timed get up and go assessments. The systems and methods described herein may be used to diagnose a variety of conditions, but in the present disclosure, a diagnosis of sarcopenia will be described as an example, for clarity.

As described above, sarcopenia is a complex condition characterized by a degenerative loss of skeletal muscle mass, quality, and strength. However, a patient that has a small amount of lean mass (an easily measurable condition), is not necessarily sarcopenic. For example, a person who could be characterized as having a relatively low amount of lean mass (for their gender and ethnicity), may be surprisingly strong, and thus not be considered sarcopenic. Similarly, a patient could lose a considerable amount of lean mass over a defined period of time, but maintain or even increase in strength, and thus not be considered sarcopenic. Conversely, a significant loss of lean mass along with an attendant loss of muscle strength could indicate sarcopenia. As such, for an accurate diagnosis of sarcopenia, both an objective measurement of lean mass and a functional measurement of muscle strength or performance are desirable.

Objective and functional measurements can also be helpful in other diagnoses. In one example, a patient may be faking or exaggerating a physical condition in order to obtain medication or other restricted treatment. More specifically, a patient may fake or exaggerate physical weakness in order to obtain strength-enhancing medications or steroids. In such a case, a functional measurement combined with an objective measurement may help prevent abuse of medications or treatments. Prior systems, however, do not correlate both objective and functional data so as to enable an accurate diagnosis.

Additionally, certain types of objective measurements can vary depending on, e.g., age, ethnicity, gender, etc. As such, to make an accurate diagnosis, a clinician is often required to consult information specific to a relevant patient population and compare specific patient data to that of the population. This may also be the case with functional information where men are generally physically stronger than women of a similar age. As such, analysis of the information required for accurate sarcopenic diagnosis is extremely complex, and arrival at an accurate diagnosis can be very time-consuming and fraught with opportunities for misinterpretation of complex data.

Systems and methods for determining physiological states via a body scan are described above. Scanning densitometers and DXA machines can determine various characteristics and volumes of a patient's body composition, such as BMD, lean mass (including whole body lean mass and appendicular lean mass), adipose tissue, visceral fat, fat mass index, and so on. Certain of these characteristics and volumes can be depicted as visual representations of information, as depicted in FIGS. 4 and 6A, above. However, such representations display information as presented locally within the body (for example, FIG. 4 depicts an image of a patient and the relative amounts of fat and lean mass at various locations within the body). Such representations do not necessarily lend themselves to the types of complex diagnoses described herein. This is a common limitation of other systems and machines that obtain objective measurements of a patient's physiological conditions such as MRI, CT scans, BIA, etc. Those systems capture information and may present such information in the form of images and measurements. However, complex conditions such as sarcopenia necessitate consideration of a significant number of factors as described above. The information presented by such an objective measurement device does not necessarily provide a complete picture of patient health for an accurate diagnosis.

Functional measurements may be obtained by various types of measuring instruments, as described above. Regardless of the type of functional measurement used, the data obtained therefrom may be collected and stored for further processing as described below. Moreover, since the equipment utilized to obtain functional measurements are typically less costly than that required to obtain an objective measurement (a dynameter is less expensive than a DXA machine, for example), it may be desirable to take functional measurements on a number of instruments for comparison or other purposes. The data associated with these multiple tests may be collected and stored for later use.

The system for diagnosing complex conditions also includes software that processes the information obtained by both the objective measurement system and the functional measurement system. The software may be resident on the objective measurement device, the functional measurement device, or may be stand alone on a remote computer. The software can include a population database that stores objective and functional measurements specific to particular populations. Alternatively, the software may access this information remotely. Databases of normal values for a subject population may be based on one or more of ethnicity/race, gender, age, relative age (young or old), relative health (normal or abnormal), etc. Normal values typically reflect various measurements of subject populations that do not display sarcopenia. These measurements can include lean mass, appendicular lean mass, and other measurements that may be determined by procedures performed with a DXA machine. The data may be raw, or be scaled, e.g., by dividing the appendicular lean mass by the square of a subject's height, or by using the subject's body mass index (BMI).

Figure 8:
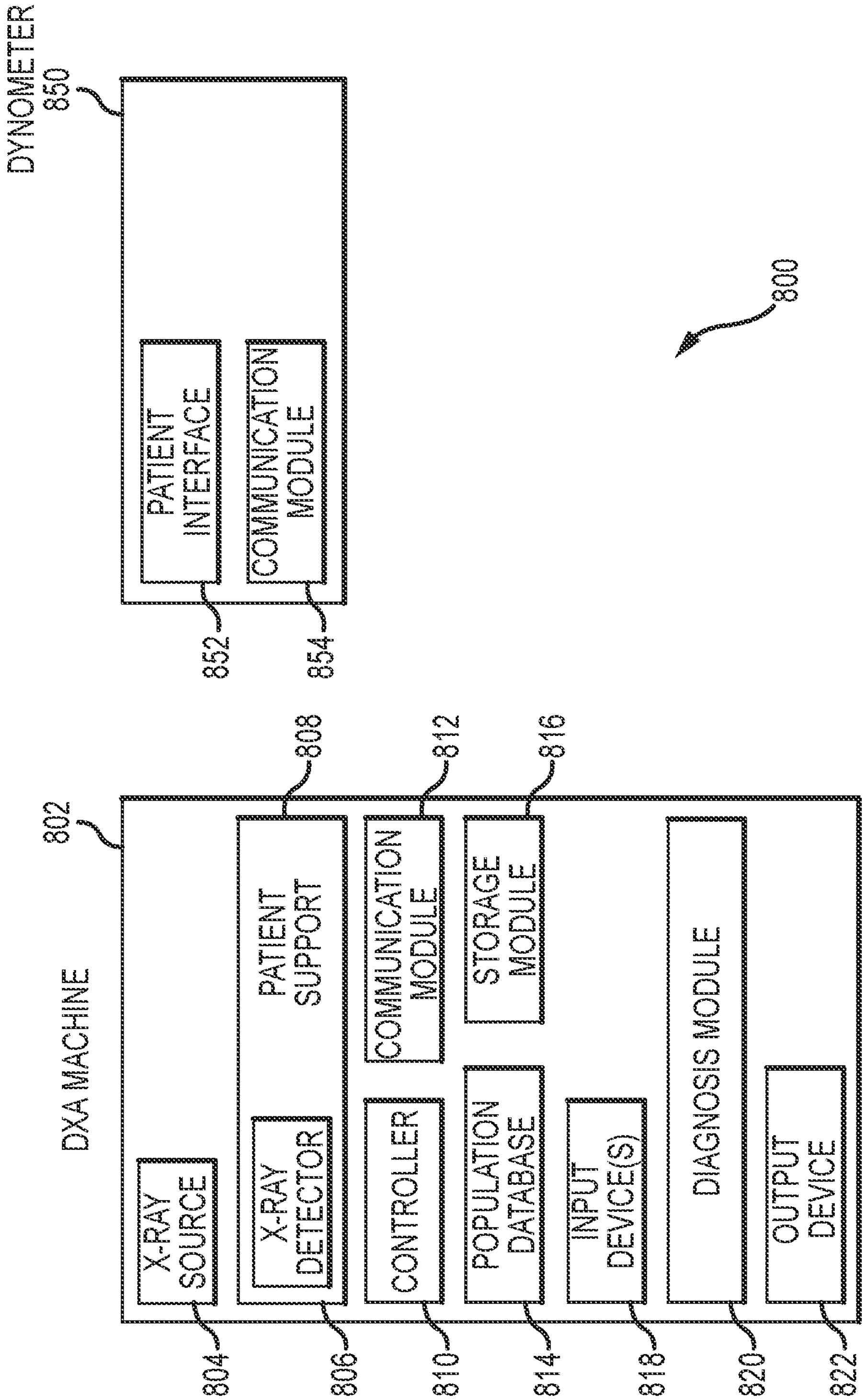
FIG. 8 depicts a system for diagnosing a complex medical condition.

In a specific example, FIG. 8 depicts a system 800 for diagnosing a complex medical condition, such as sarcopenia. Here, a DXA machine 802 is the primary component on which the diagnosis system 800 operates. The DXA machine 800 may be the type as described herein. Additionally, the DXA machine may include a number of additional modules and components that may be utilized to perform the complex diagnoses described herein. Not every component of the DXA machine 802 is depicted in FIG. 8. The DXA machine 802 includes standard components such as an x-ray source 804 and an x-ray detector 806 (which may be disposed in a patient support 808 such as a table). A controller 810 controls the functions and operation of the various components and hardware/software modules. A communication module 812 allows for communication with various remote components, for example, the depicted functional measurement instrument 850 (e.g., a dynameter), a hospital network, and so on. The communication module can function via wired or wireless communication, BlueTooth, WiFi, and so on. A population database 814 (that contains information regarding "normal" objective and functional measurements of subject populations based on age, ethnicity, and other categories) can be local to the DXA machine 802 or remote therefrom (and accessed via the communication module 812).

The DXA machine 802 also includes a storage module 816 that stores patient data (age, ethnicity, other vital characteristics, objective measurements, functional measurements, and so on). Of course, such information may be stored remotely (e.g., in a hospital network) and accessed via the communication module 812. The DXA machine 802 can also include one or more input devices 818, such as keyboards, graphic user interfaces, etc. A diagnosis module 820 performs the required analysis of the data obtained from the population database 814 and storage module 816 (e.g., the patient-specific information), and prepares the output reports described below. In other example, the diagnosis module 820 may also be contained on a remote computer (e.g., connected to a hospital network) and the analysis performed remote from the DXA machine 802. An output device 822 may include a printer and/or a display screen for generating the output reports for review by the clinician. Paper reports prepared by a printer may be particularly useful since they may be delivered to the patient in a different location for explanation and discussion.

The dynameter 850 or other functional measurement device may include a patient interface 852 (e.g., the portion that the patient squeezes) as well as a communication module 854 to deliver the obtained data to the communication module 812 of the DXA machine 802, or to a remote computer. Given the simplified nature of many functional measurement devices, the data obtained therefrom may also be entered directly to the DXA machine 802 (e.g., the diagnosis module 820) via the input device 818. Indeed, for certain performance tests that include timed performance (e.g., timed get up and go assessments), manual entry via the input device 818 may be the preferred method of entering the functional measurements.

Returning to the functionality of the diagnosis module 820, given the amount of population data available to a clinician, it would be extremely difficult, if not impossible, to compare a patient's data to the subject population dataset. Indeed, as described above, the subject population can be portioned based on categories such as ethnicity, age, and gender. For a clinician, then, to derive clinically-valuable information from the data, the clinician must be able to quickly compare the patient data to that of the population. Moreover, simply comparing patient information to a list or table may not be the most clinically-relevant way to relay the results of the tests. As such, the technologies described herein visually depict patient information on a graph or plot that is scaled to the appropriate population dataset, so as to enable meaningful, immediate comparisons and diagnoses.

FIGS. 9A-9D depict exemplary plots for a complex condition diagnosis, such as a sarcopenic diagnosis. In general, the information is displayed as a two-dimensional graph 900 having scores for the objective measurement, e.g., lean muscle mass from a DXA machine plotted on a horizontal axis 902*a*, while the functional measurement, e.g., grip strength, is plotted on a vertical axis 904*a*, in this example. Thus, the information so presented is able to be quickly understood by the clinician, and in a format that is easy for the clinician to explain to a patient.

Figure 9A:
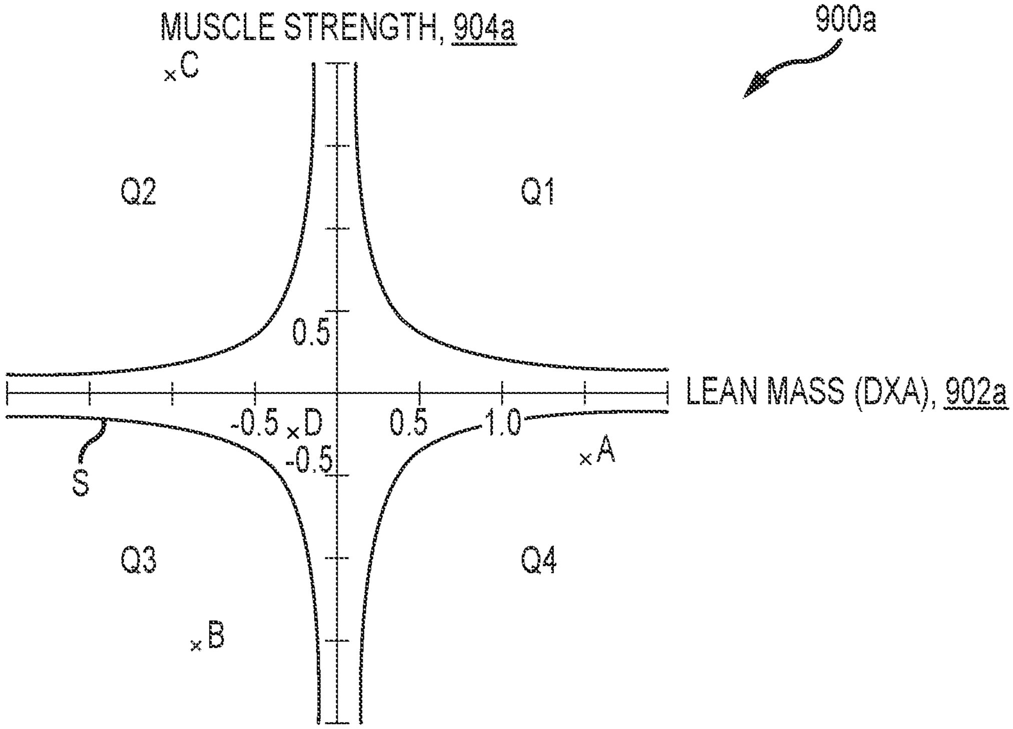
FIGS. 9A-9D depict exemplary plots for a complex condition diagnoses.

In the example depicted in FIG. 9A, patient data that appears in Quadrant Q1 would be indicative of both a high objective measurement (e.g., high lean muscle mass) and a high functional measurement (e.g., high strength). As such, the patient would be considered non-sarcopenic. Data that is plotted in Quadrant Q2 or Quadrant Q4 indicates a low score in either lean muscle mass or muscular strength, respectively. Data plotted in Quadrant Q4, for example, at data point A, would indicate that the patient has a high lean muscle mass but a low muscular strength. Such findings can be important, as this may mean that the patient had some trouble with the functional test and a different functional test might be appropriate. For example, a patient that is arthritic (diagnosed or undiagnosed) may have trouble with a grip strength test, but may be able to perform a leg press or gait speed test with little or no problems. As a result of the information plotted on the graph, and the possibly inconsistent nature of the results (high muscle mass correlated with weak strength) the clinician may order a different functional test, or use data from a different functional test, if available. If the results, e.g., of a leg press, again indicate muscle weakness, the clinician may prescribe an exercise regimen to build strength, as opposed to a medication or steroid. Additionally, data point A might indicate that the patient was not exerting sufficient effort during the functional test in an effort to convince the clinician of their need for medicinal treatment. As such, a clinician can quickly determine from the presented information that the patient is not a proper candidate for a more aggressive form of treatment. Data plotted in Quadrant Q2 can result in similar conclusions.

Data plotted in Quadrant Q3, for example at data point B, would be indicative of both low muscle mass and low strength. As such, data presented here may be indicative of a patient with sarcopenia. A particular patient's data may be presented on the graph 900*a* as a Z-score, which depicts how many standard deviations a subject score may be away from others in their population dataset (e.g., age and gender). Thus, if the patient's data is a significant number of standard deviations away from that of the population, this information may be quickly understood. The visual display of a patient data point is also useful because it allows a clinician to quickly identify potentially problematic results quickly. For example, with regard to patient data points C and D on FIG. 9A, although data point C might appear problematic, due to the significant standard deviation from the norm on lean muscle mass, the considerably elevated muscle strength data should quickly allay any concerns on the part of a clinician. Conversely, although data point D is fewer standard deviations away from the norms with regard to both objective and functional measurements, the fact that data point D is closer to the sarcopenic range identified by curve S will quickly signal to the clinician that aggressive treatment and intervention may be desirable.

Figure 9B:
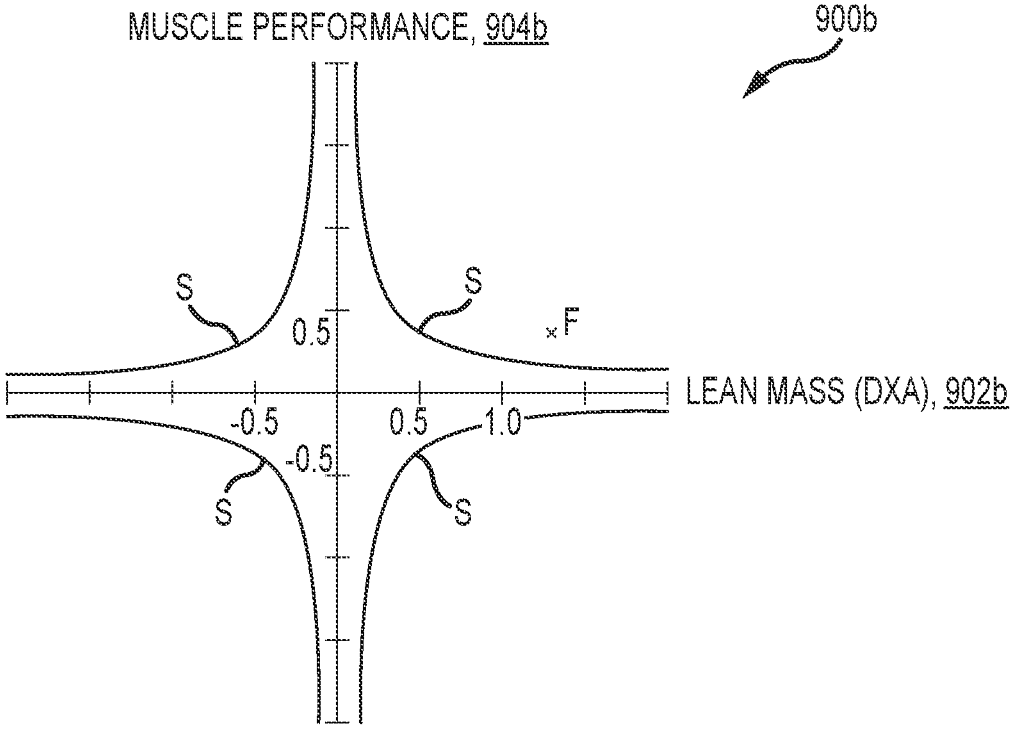
Figure 9C:
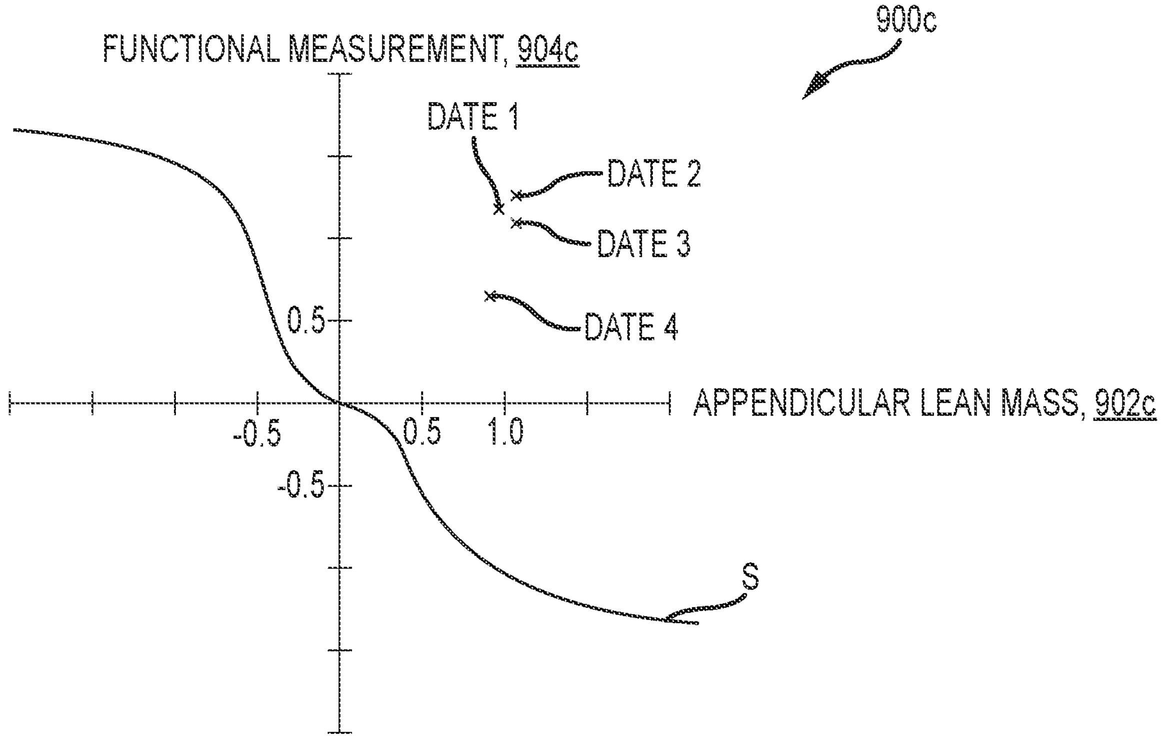
Figure 9D:
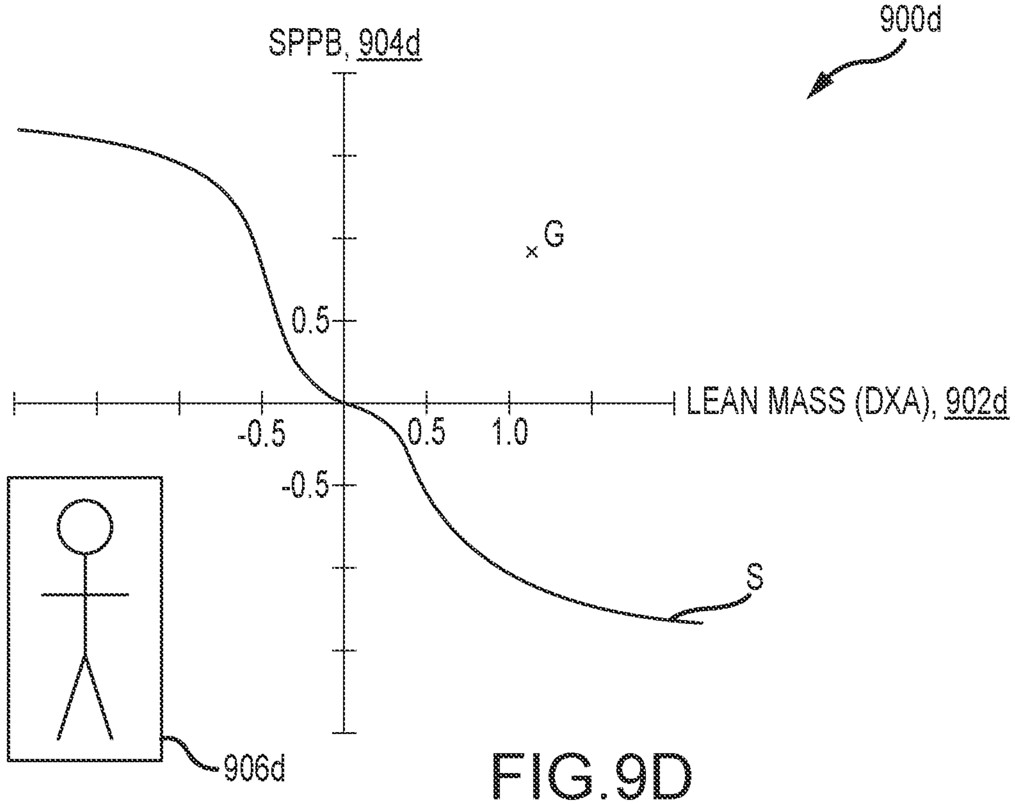

FIGS. 9B-9D depict different graphic representations 900*b*-900*d* for presenting information regarding objective and functional measurements. In FIG. 9B, for example, muscle performance is used as the performance-based metric on the y-axis 904*b*, while an objective measurement of lean mass obtained from a DXA system is depicted on the x-axis 902*b*. The term "muscle performance" represents another functional measurement that may be compared to normal levels within a particular population. Muscle performance could, e.g., be measured by get-up and go, SPBB, etc. In general, the type of functional test is not particularly relevant, only that a functional measurement is correlated with an objective measurement such that the information can be clearly conveyed to a clinician. Again, one or more curves S that represent particular ranges of diagnoses may be presented on the graph 900*b*, as may the data point (e.g., data point F) that represents the patient's objective and functional measurements.

FIGS. 9C and 9D depict other graphical representations 900*c*, 900*d*, again, having a functional measurement on the y-axis 904*c*, 904*d*, with an objective measurement on the x-axis 902*c*, 902*d*. A reference curve S can also be applied to the graph 900*c*, 900*d* and can take any shape or configuration that is diagnostically relevant to the clinician.

Other information may be presented on the graphical representations. For example, FIG. 9C depicts historical patient data at Dates 1-4 (which may indicate an increase or decrease in objective and/or functional measurements). The historic patient data includes both objective and functional measurement data as that data was obtained on Dates 1-4. In the depicted plot 900*c*, data obtained on Dates 1-3 is fairly consistent, while the significant drop in the functional measurement on Date 4 may indicate a problem to the clinician. Such a significant change may be indicative of a condition that may necessitate intervention. In another example, if the drop is explainable (e.g., reduction in a functional performance measurement due to an unrelated injury), the clinician may disregard the results and order a different functional performance assessment.

FIG. 9D depicts another graphical representation in a plot 900*d*. As with the previous examples, a functional measurement is presented on the y-axis 904*d*, with an objective measurement on the x-axis 902*d*. A reference curve S may also be presented, along with patient data information (e.g., at data point G). Additionally, an image 906*d* of a body scan (such as the body composition map depicted in FIG. 4) may be depicted along with the graphical representation of plot 900*d*. Alternatively or additionally, an image that depicts relative differences in muscle mass of individual limbs so as to determine muscle symmetry, may also be presented. With such an image, information regarding dominant and non-dominant arm and leg measurements for symmetry may be presented. Additionally, information regarding hydration levels can be presented. Multiple images (taken over a predetermined time period of weeks, months, or years) may also be valuable for a clinician to show development or degeneration of skeletal muscles in geriatric or even pediatric patients. Such images are another example of historical data that may be presented, similar to the historical data depicted in FIG. 9C. Although sarcopenia, osteoporosis, and other conditions are generally associated with geriatric patients, the technologies described herein are not limited to diagnosis of only geriatric patients, but instead can provide useful diagnostic information for patients of all ages.

Figure 10:
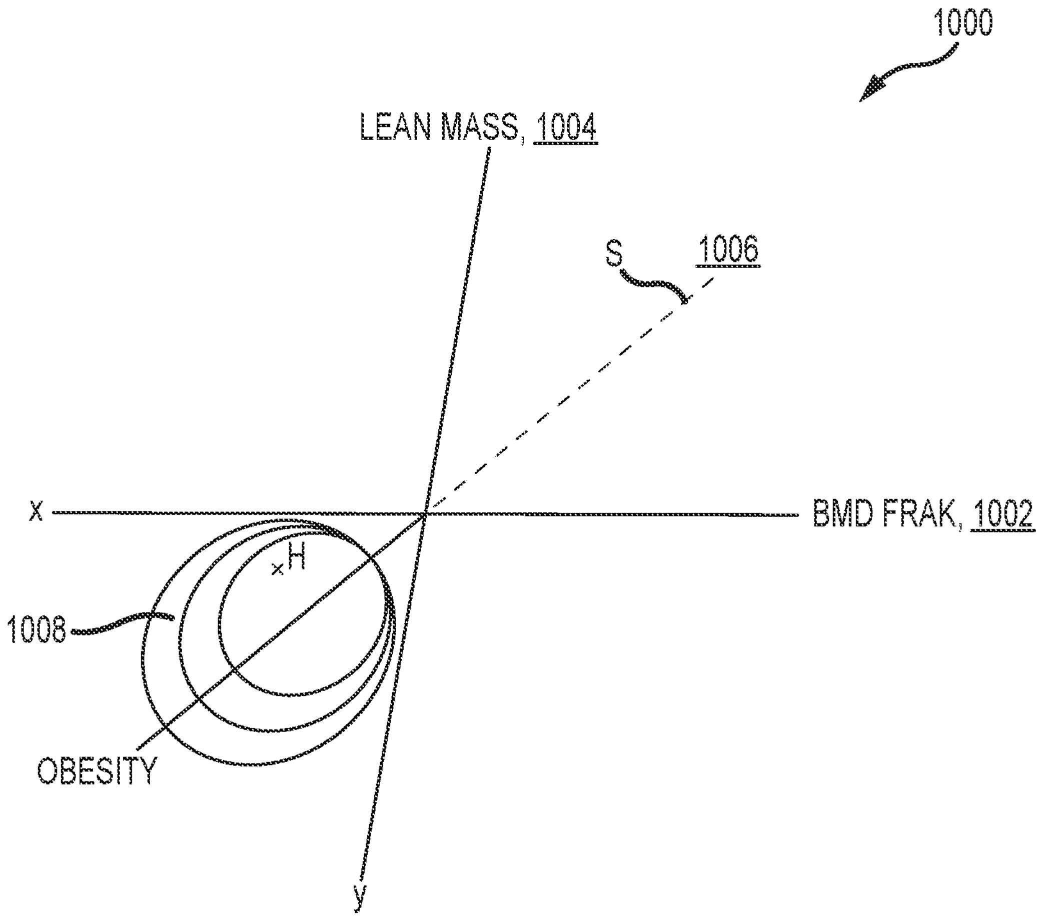
FIG. 10 depicts another example of a plot for complex condition diagnosis.

Additional plots can be utilized for quick analysis of correlated data associated with a patient. For example, FIG. 10 depicts a three-dimensional coordinate system plot 1000 where bone mass density (BMD) or probability of bone fracture risk (FRAX) is plotted on the x-axis 1002. FRAX is also related to osteoporosis. Lean muscle mass is plotted on the y-axis 1004, while obesity is plotted on the z-axis 1006. Standard deviations from the norm may also be identified on each axis 1002, 1004, 1006, such as depicted above in FIGS. 9A-9D. As such, three objective measures are plotted, which may be helpful in determining a patient diagnosis of the frailty syndrome, which includes associated weakness, slowing, decreased energy, lower activity, weight loss, etc. As such, frailty is also a complex condition that can benefit from the information visually presented in the forms described herein. A volume 1008 that indicates information similar to the curve of FIGS. 9A-9D may be presented on the plot 1000. Such a volume 1008 may be indicative of data sets for the population who have been diagnosed with frailty syndrome, so as to provide a comparison for the data obtained from a particular patient (e.g., data point H). This three-dimensional coordinate system plot 1000 may be particular advantageous when displayed on an output device such as a display screen, as opposed to being printed in a two-dimensional medium (e.g., paper). The system plot 1000 may be rotated or otherwise manipulated to determine whether the patient data point H actually lies within the volume 1008, which may indicate a frailty syndrome diagnosis.

Figure 11A:
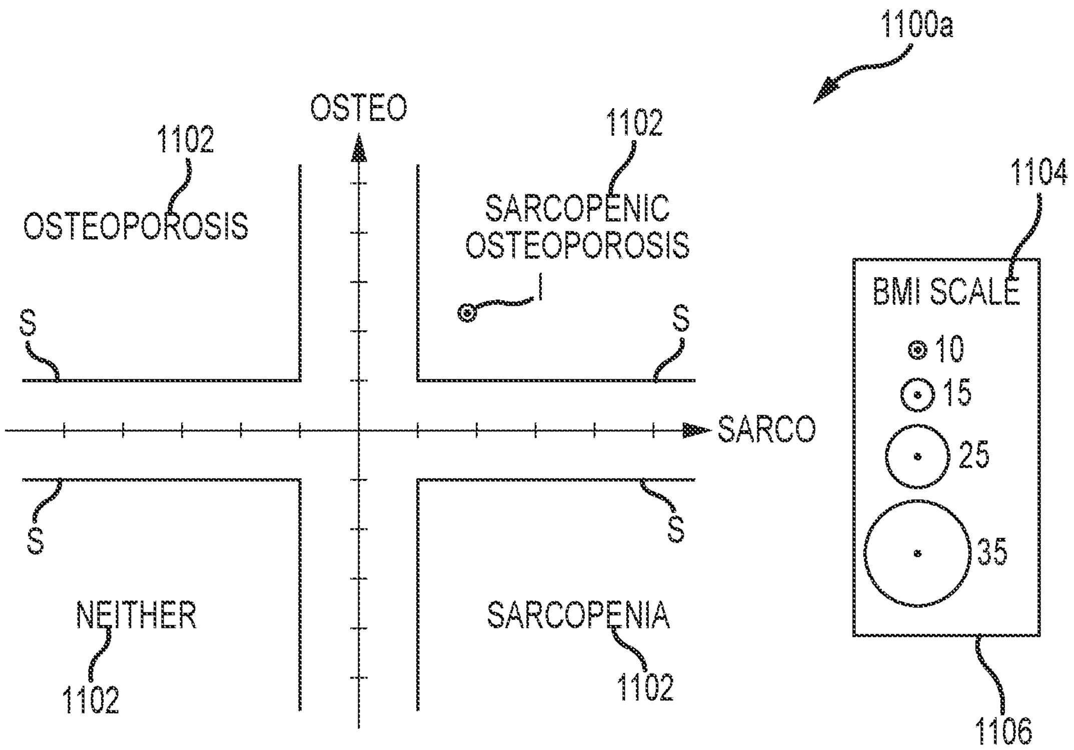
FIGS. 11A-11B depict other examples of plots for a complex condition diagnoses.
Figure 11B:
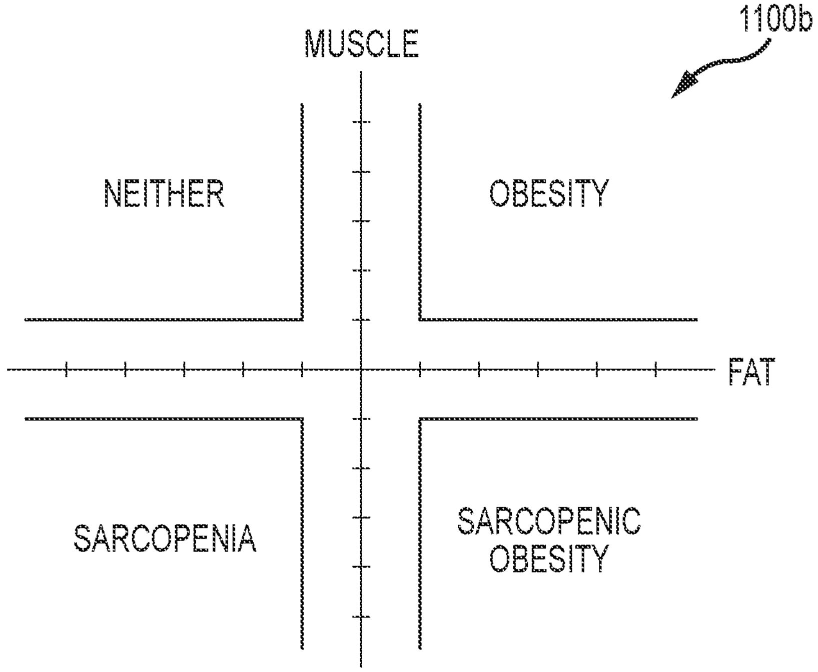

Given the potential limitations of the three-dimensional plot of FIG. 10, other types of plots that display complex data in a two-dimensional medium are also contemplated. FIGS. 11A and 11B, for example, depict other coordinate system plots 1100*a*, 1100*b* for plotting data related to complex physiological conditions. Again, information presented in these visual representations can enable a clinician to quickly diagnose a patient and communicate to a patient information relevant to their health. In FIG. 11A, information related to sarcopenia and osteoporosis are plotted and can indicate whether a patient suffers from sarcopenia, osteoporosis, a combined condition, or neither. Labels 1102 identifying the conditions indicative of each quadrant Q1-Q4 can be identified as depicted, as well as curves S representing population data sets. The data point I depicted in FIG. 11A can be scaled to denote severity of a condition, which in this case shows the body mass index (BMI). The scale 1104 may be presented in an associated display area 1106, much like the display area depicted in FIG. 9D. In FIG. 11B, muscle mass and fat mass can be plotted on plot 1100*b* so as to determine quickly whether a patient is obese, sarcopenic, or both. As such, although diagnosis based on objective measurements and functional measurements are described as advantageous for diagnosis of certain complex conditions, multiple objective measurements may also be utilized.

The various plots depicted herein can be printed to paper or presented on an output device such as the display screen depicted in FIG. 8. If displayed, a touch screen may be utilized to expand the information presented on the plots. For example, as described above, patient data points are presented on a plot. If further information about the data point, representative plot scale, etc., is desired, those components may be selected or hovered over with a mouse or selection element, and further information presented. Historic patient data can be hidden and unhidden, along with trending information and the like. Display of the plots on a display screen and the manipulation of the plots and associated data as described above may be particularly advantageous for the more complex three-dimensional plots of FIG. 10, for example.

Figure 12:
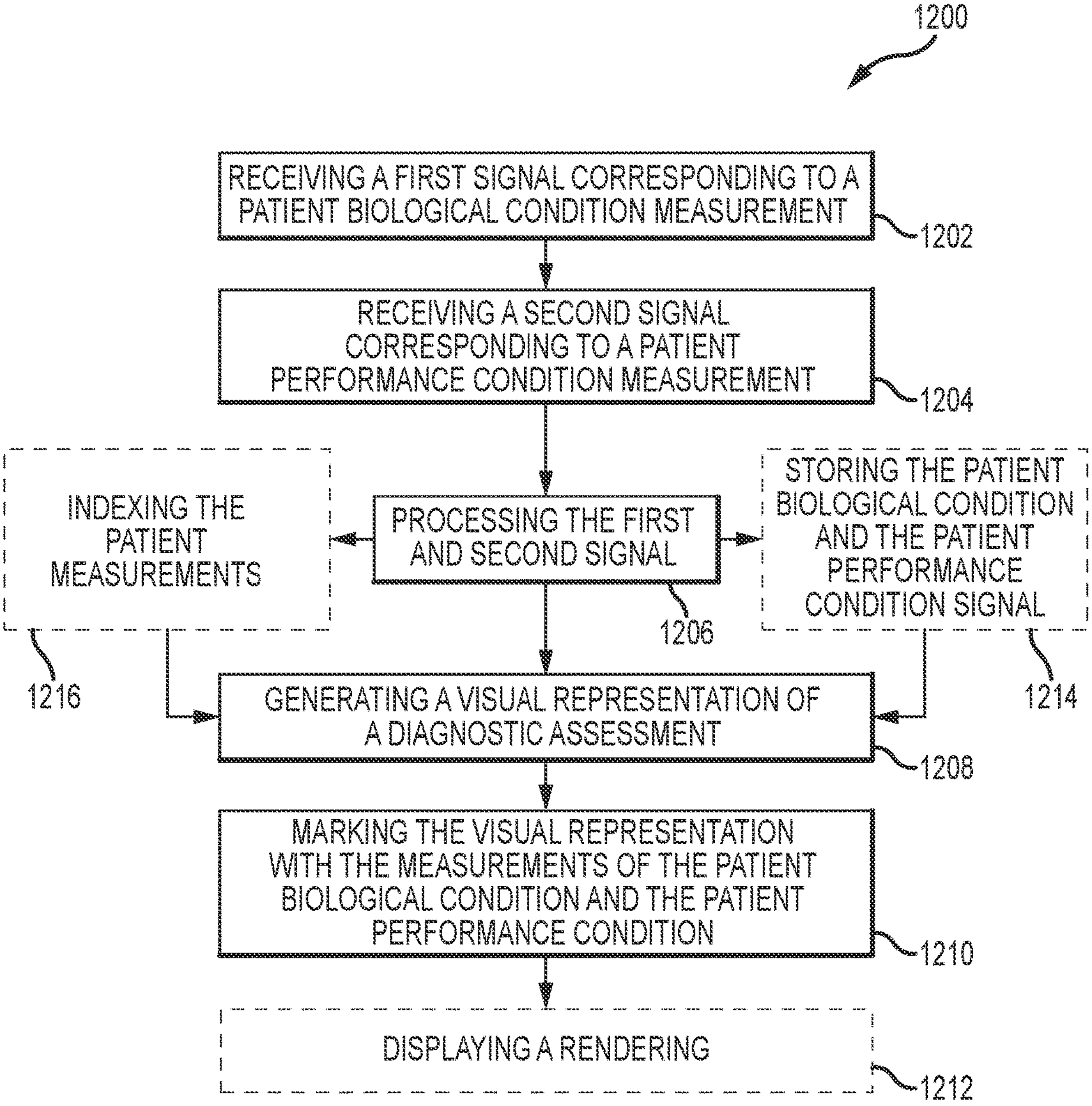
FIG. 12 depicts a method of generating a visual representation of a complex medical diagnosis.

FIG. 12 depicts a method 1200 of generating a visual representation of a complex medical diagnosis. The method 1200 begins with operation 1202, receiving a first signal that corresponds to a measurement of a patient biological condition, which may be one of the objective measures described above. In operation 1204, a second signal that corresponds to a measurement of a patient performance condition is received. Again, examples of such performance measurements are described above. The first and second signals are processed in operation 1206, which may include categorization of the objective measurement and performance measurement, confirmation that the signals are valid, or other factors. In a basic operation of the method, a visual representation of a diagnostic assessment is generated in operation 1208. This visual representation may be a two-dimensional or three-dimensional plot, such as depicted above. A first axis of the plot would correspond to the patient biological condition, while a second axis of the plot would correspond to the patient performance condition in a two-axis example. In operation 1210, the plot of the visual representation is marked or displayed with the measurements of the patient biological condition and the patient performance condition. The basic operations of the method 1200 may be sufficient to display a visual representation of a complex medical diagnosis. However, additional operations may be performed that add additional context to the visual assessment to more accurately represent the diagnosis.

In optional operation 1212, for example, a rendering that corresponds to the patient biological condition may be simultaneously displayed with the visual representation. Returning to operation 1206, such processing may also include storage of the patient biological condition measurement and/or the patient performance condition measurement, operation 1214. Storage of repeated measurements generates a historical database of patient measurements, which may be advantageous to track a patient condition over a long term. This historical data may then be accessed and utilized in conjunction with the visual representation generated in operation 1208 to mark historical measurements thereon, e.g., as performed in operation 1210.

Again returning to the processing operation 1206, processing may also include indexing the patient measurements, operation 1216, for example against a data set. Such data sets may include population data sets matched to the patient (that is, corresponding to one or more of the patient's age, gender, ethnicity, and so on). The indexing operation 1216 is valuable in that it compares the patient measurements to data sets containing potentially similar measurements obtained from a population. The data sets may be stored remotely or locally and accessed and processed. Processing may include selecting particular information from the population data set. For example, if the patient's functional measurement was a timed get up and go test, only data entries that include get up and go testing would be selected. Based on the data obtained from the population data set, a curve representing, e.g., threshold conditions, may be generated. This curve may be marked or displayed on the visual representation to provide further information as to the patient's condition or diagnosis relative to the population. Thus, when the patient measurements are marked or displayed on the visual representation in operation 1210, they are indexed against this curve.

Figure 13:
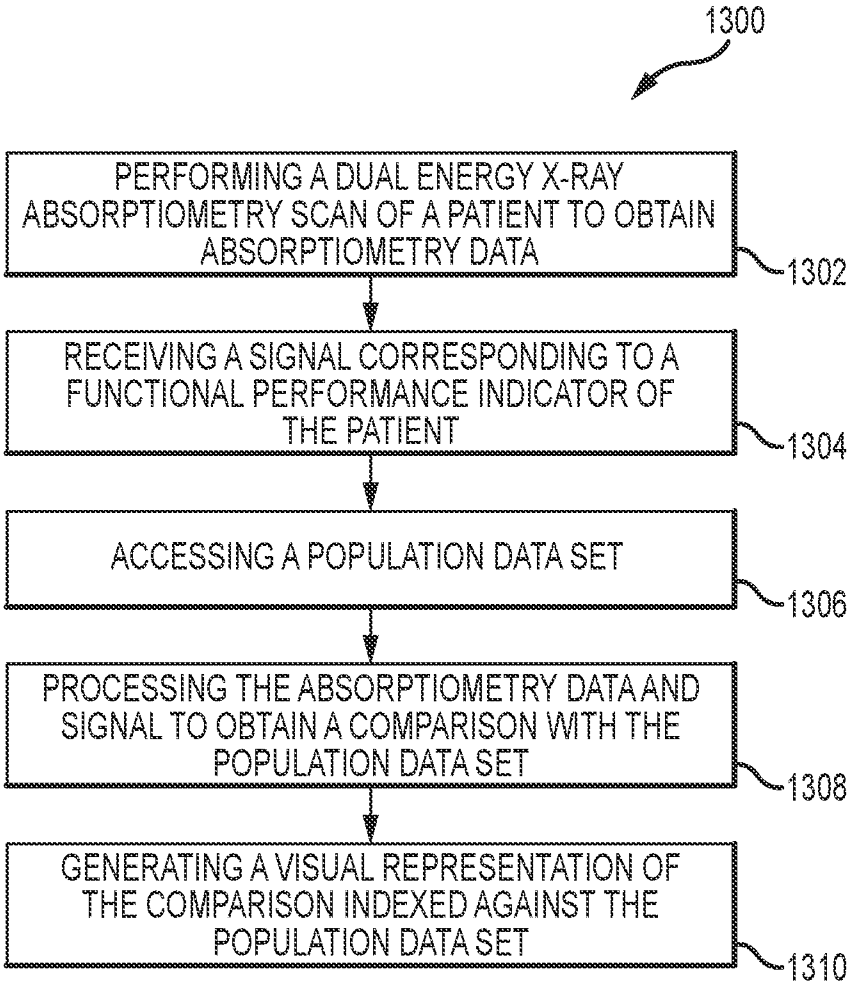
FIG. 13 depicts another method of generating a visual representation of a complex medical diagnosis.

FIG. 13 depicts another method 1300 of generating a visual representation of a complex medical diagnosis, more specifically, in the context of utilizing a DXA machine to obtain the objective measurement. The method 1300 begins with performing a dual energy x-ray absorptiometry scan of a patient (or at least a portion thereof) using a dual-energy absorptiometry system so as to acquire a plurality of dual energy x-ray absorptiometry data, operation 1302. In operation 1304, a signal corresponding to a functional performance indicator of the patient is received. This signal may correspond to the results of one or more performance based tests or assessments of the patient, e.g., a short physical performance battery, handgrip strength, gait speed, timed get up and go, standing balance, and/or fall proclivity. A population data set, which may be age-matched, gender-matched, and/or ethnicity-matched with the patient, is accessed in operation 1306. In operation 1308 the plurality of dual energy x-ray absorptiometry data and the signal corresponding to the functional performance indicator are processed, for example, by a computer. This processing operation 1308 obtains a comparison to the at least one population data set accessing in operation 1306. The processing operation of operation 1308 may include computer processing the plurality of dual energy x-ray absorptiometry data to determine an estimate of the patient's body composition, the patient's bone mineral density, the patient's muscle mass, and/or the patient's adipose tissue (all objective measurements). In operation 1310 a visual representation of the comparison indexed against the at least one population data set is generated. This may include generating at least one of a report of the comparison indexed against the at least one population data set, a visual representation of the comparison indexed against the at least one population data set, a report depicting a colorized body composition map of the patient, and a report depicting asymmetrical muscle mass in a patient's limbs. The representation may be printable or displayed, either at the device that performed the dual energy x-ray absorptiometry scan or remotely.

Figure 14:
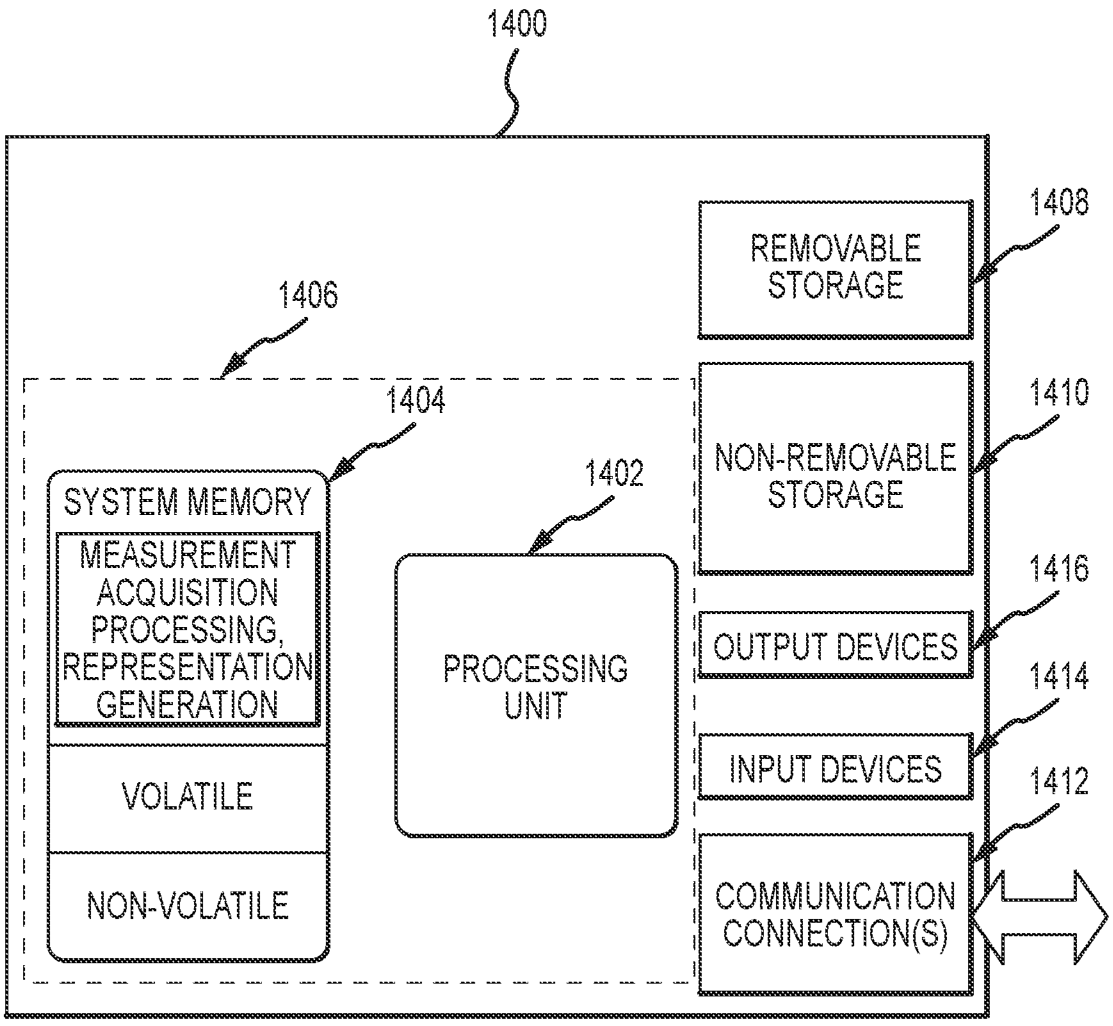
FIG. 14 illustrates one example of a suitable operating environment in which one or more of the present examples can be implemented.

FIG. 14 illustrates one example of a suitable operating environment 1400 in which one or more of the present examples can be implemented. This operating environment may be incorporated directly into a scanning system, or may be incorporated into a computer system discrete from, but used to control, a scanning system such as described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1400 typically includes at least one processing unit 1402 and memory 1404. Depending on the exact configuration and type of computing device, memory 1404 (storing, among other things, instructions to perform the measurement acquisition, processing, and visual representation generation methods disclosed herein) can be volatile (such as RAM), non-volatile (such as ROM, flash memory, etc.), or some combination of the two. This most basic configuration is illustrated in FIG. 14 by dashed line 1406. Further, environment 1400 can also include storage devices (removable, 1408, and/or non-removable, 1410) including, but not limited to, magnetic or optical disks or tape. Similarly, environment 1400 can also have input device(s) 1414 such as touch screens, keyboard, mouse, pen, voice input, etc., and/or output device(s) 1416 such as a display, speakers, printer, etc. Also included in the environment can be one or more communication connections 1412, such as LAN, WAN, point to point, Bluetooth, RF, etc.

Operating environment 1400 typically includes at least some form of computer readable media. Computer readable media can be any available media that can be accessed by processing unit 1402 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1400 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein comprise such modules or instructions executable by computer system 1400 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 1400 is part of a network that stores data in remote storage media for use by the computer system 1400.

Figure 15:
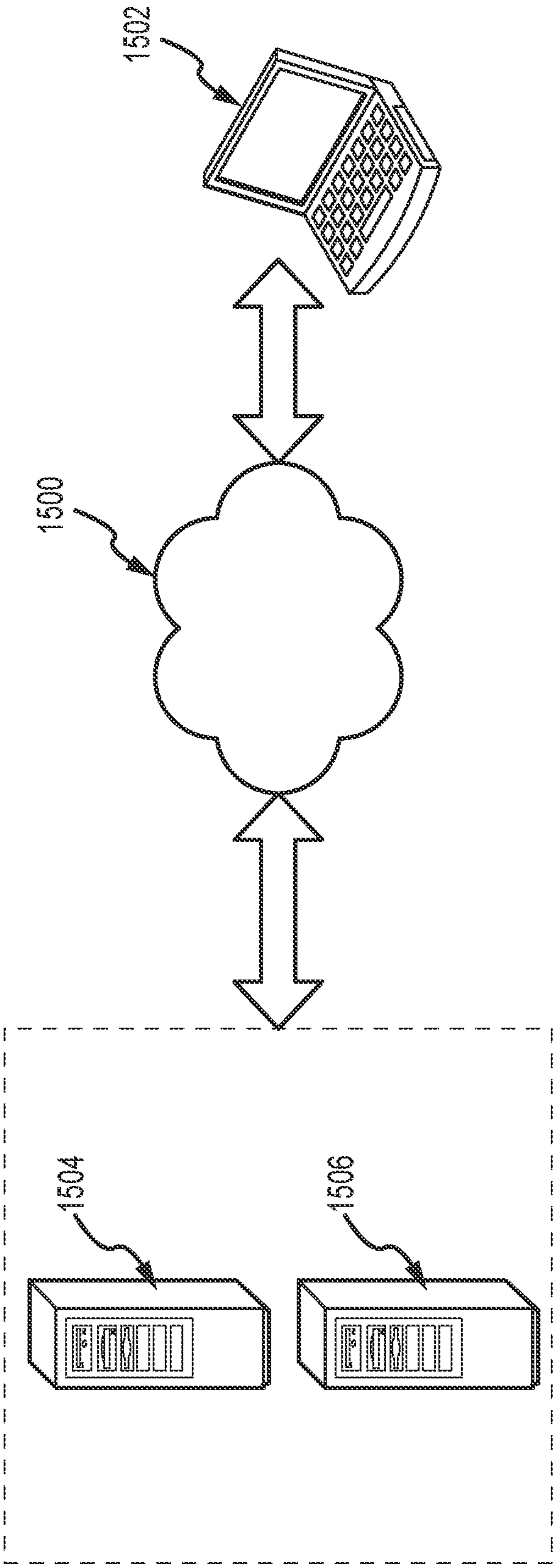
FIG. 15 is an embodiment of a network in which the various systems and methods disclosed herein may operate.

FIG. 15 is an example of a network 1500 in which the various systems and methods disclosed herein may operate. In examples, a client device, such as client device 1502, may communicate with one or more servers, such as servers 1504 and 1506, via a network 1508. In examples, a client device may be a laptop, a personal computer, a smart phone, a PDA, a netbook, or any other type of computing device, such as the computing device in FIG. 14. In examples, servers 1504 and 1506 may be any type of computing device, such as the computing device illustrated in FIG. 14. Network 1508 may be any type of network capable of facilitating communications between the client device and one or more servers 1504 and 1506. Examples of such networks include, but are not limited to, LANs, WANs, cellular networks, and/or the Internet.

In examples, the various systems and methods disclosed herein may be performed by one or more server devices. For example, in one example, a single server, such as server 1504 may be employed to perform the systems and methods disclosed herein, such as the method for scanning and image processing. Client device 1502 may interact with server 1504 via network 1508. In further examples, the client device 1502 may also perform functionality disclosed herein, such as scanning and image processing, which can then be provided to servers 1504 and/or 1506.

In alternate examples, the methods and systems disclosed herein may be performed using a distributed computing network, or a cloud network. In such examples, the methods and systems disclosed herein may be performed by two or more servers, such as servers 1504 and 1506. Although a particular network example is disclosed herein, one of skill in the art will appreciate that the systems and methods disclosed herein may be performed using other types of networks and/or network configurations.

The examples described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the invention may also combine elements or components of those that are disclosed in general but not expressly exemplified in combination, unless otherwise stated herein. The scope of the technology is defined by the following claims and any equivalents therein.

What is claimed is:

1. A method comprising:

performing a dual energy x-ray absorptiometry scan of at least a portion of a patient using a dual-energy absorptiometry system to acquire a plurality of dual energy x-ray absorptiometry data;

receiving a signal corresponding to a functional performance indicator of the patient;

accessing from a computer database at least one population dataset;

computer-processing the plurality of dual energy x-ray absorptiometry data and the signal corresponding to the functional performance indicator to obtain a comparison to the at least one population data set; and generating a visual representation of the comparison indexed against the at least one population data set, the visual representation including a curve illustrating the comparison to the at least one population dataset, the curve plotting dual energy x-ray absorptiometry data with respect to the functional performance indicator.

2. The method of claim 1, wherein the computer-processing step comprises computer processing the plurality of dual energy x-ray absorptiometry data to determine an estimate of the patient's body composition.

3. The method of claim 1, wherein the computer-processing step comprises computer processing the plurality of dual energy x-ray absorptiometry data to determine an estimate of the patient's bone mineral density.

4. The method of claim 1, wherein the computer-processing step comprises computer processing the plurality of dual energy x-ray absorptiometry data to determine an estimate of the patient's muscle mass.

5. The method of claim 1, wherein the computer-processing step comprises computer processing the plurality of dual energy x-ray absorptiometry data to determine an estimate of the patient's adipose tissue.

6. The method of claim 1, wherein the received signal corresponds to a result of a short physical performance battery assessment of the patient.

7. The method of claim 1, wherein the received signal corresponds to a handgrip strength assessment of the patient.

8. The method of claim 1, wherein the received signal corresponds to a gait speed assessment of the patient.

9. The method of claim 1, wherein the received signal corresponds to a timed get up and go assessment of the patient.

10. The method of claim 1, wherein the received signal corresponds to a standing balance assessment of the patient.

11. The method of claim 1, wherein the received signal corresponds to a fall proclivity assessment of the patient.

12. The method of claim 1, wherein the accessing step comprises accessing at least one of an age matched population data set, a gender matched population data set, and an ethnicity matched population data set.

13. The method of claim 1, wherein the generating step comprises generating at least one of a printable report of the comparison indexed against the at least one population data set, a report depicting a colorized body composition map of the patient, and a report depicting asymmetrical muscle mass in a patient's limbs.

14. The method of claim 1, wherein the curve illustrates standard deviations compared to the at least one population dataset.

* * * * *